(12) United States Patent
Agostinetto et al.

(10) Patent No.: US 8,664,369 B2
(45) Date of Patent: Mar. 4, 2014

(54) LH LIQUID FORMULATIONS

(75) Inventors: Rita Agostinetto, Rocca di Papa (IT);
Fabrizio Samaritani, Rome (IT);
Alessandra Del Rio, Rome (IT); Joel Richard, Montfort l'Amaury (FR)

(73) Assignee: Merck Serono S.A., Geneva (CH)

( * ) Notice: Subject to any disclaimer, the term of this patent is extended or adjusted under 35 U.S.C. 154(b) by 658 days.

(21) Appl. No.: 12/681,688

(22) PCT Filed: Oct. 29, 2008

(86) PCT No.: PCT/EP2008/064679
§ 371 (c)(1),
(2), (4) Date: Jun. 17, 2010

(87) PCT Pub. No.: WO2009/056569
PCT Pub. Date: May 7, 2009

(65) Prior Publication Data
US 2010/0261649 A1 Oct. 14, 2010

Related U.S. Application Data

(60) Provisional application No. 61/004,481, filed on Nov. 28, 2007.

(30) Foreign Application Priority Data

Nov. 1, 2007 (EP) .................................... 07119832

(51) Int. Cl.
*C07K 14/59* (2006.01)
*C07K 7/23* (2006.01)
*A61K 38/09* (2006.01)
*A61K 38/24* (2006.01)

(52) U.S. Cl.
USPC ............ 530/398; 530/350; 514/10.1; 514/9.8

(58) Field of Classification Search
None
See application file for complete search history.

(56) References Cited

U.S. PATENT DOCUMENTS

| | | | |
|---|---|---|---|
| 7,741,268 B2 * | 6/2010 | Samaritani et al. | ............ 514/9.9 |
| 2004/0224886 A1 | 11/2004 | Chen | |
| 2006/0147480 A1 * | 7/2006 | Samaritani et al. | ............ 424/400 |

FOREIGN PATENT DOCUMENTS

| | | | | |
|---|---|---|---|---|
| EP | 0448146 A | | 9/1991 | |
| EP | 0974359 | * | 1/2000 | ............ A61K 38/24 |
| NL | EP09853945 | * | 7/1996 | ............ A61K 38/24 |
| WO | WO93/11788 | * | 6/1993 | ............ A61K 37/38 |
| WO | WO 96/29095 | * | 9/1996 | ............ A61K 47/26 |
| WO | WO2004/087213 | * | 10/2004 | ............ A61K 47/10 |

OTHER PUBLICATIONS

Filicori et al., Human Reproduction Update, 2002; 8: 543-557.*
Website downloaded Nov. 27, 2012 from: ema.europa.eu/docs/en_GB/document_library/EPAR_Scientific_Discussion/human/000292/WC500045911.pdf (2004; 16 pages total).*
The archived website downloaded Nov. 28, 2012 from: web.archive.org/web/20050209194609/http://thelabrat.com/protocols/PBST.shtml (Feb. 9, 2005; 1 p. total).*
The website downloaded Nov. 27, 2012 from: atsbio.com/catalog/protocols/p_conc.pdf. (1 page total).*
Burgues et al., Hum. Reprod. 12(5): 980-6 1987.
Cerpa-Poljak et al., Endocrinology 132(1): 351-356 1993.
Dias et al., J. Biol. Chem. 269(41): 25289-25294, 1994.
Fiddes & Talmadge, Recent Prog. Horm. Res. 40: 43-78, 1984.
Flack et al., J. Biol. Chem. 269(19): 14015-14020, 1994.
Hakola et al., Molecular and Cellular Endocrinology 127(1): 59-69, 1997.
Keene et al., J. Biol. Chem 264(9): 4769-4775, 1989.
Keutmann et al., J. Biol. Chem 264(9): 4769-4775, 1979.
Klein et al., Fertility & Sterility; 77(6): 1248-1255, 2002.
Klein et al., Human Reprod. 18(1): 50-56, 2003.
LaPolt et al., Endocrinology 131(6): 2514-2520, 1992.
Manning et al., Pharmaceutical research vol. 6, No. 11 p. 903-918, 1989.
PCT/EP2008/06479 International Search Report dated Mar. 19, 2009.
PCT/EP2008/06479 Written Opinion dated Mar. 19, 2009.
Reichart & Ramsey, J. Biol. Chem. 250(8): 3034-3040, 1975.
Shome et al., J. Clin. Endocrinol. Metab. 39(1):203-205, 1974.
Shome et al., J. Prot. Chem. 7(4): 325-339, 1988.
Steelman et al., Endocrinology;,3(6): 604-616, 1953.
Talmadge et al., Nature 307: 37-40, 1984.
Valove et al., Endocrinology;135(6): 2657-2661, 1994.
Van Hell et al., Acta Endocrinologica; 47: 409-418, 1964.

* cited by examiner

*Primary Examiner* — Bridget E Bunner
*Assistant Examiner* — Christina Borgeest
(74) *Attorney, Agent, or Firm* — Woodard, Emhardt, Moriarty, McNett & Henry LLP

(57) ABSTRACT

The invention relates to liquid pharmaceutical formulations of luteinizing hormone (LH) for single- or multi-dose administration.

15 Claims, 7 Drawing Sheets

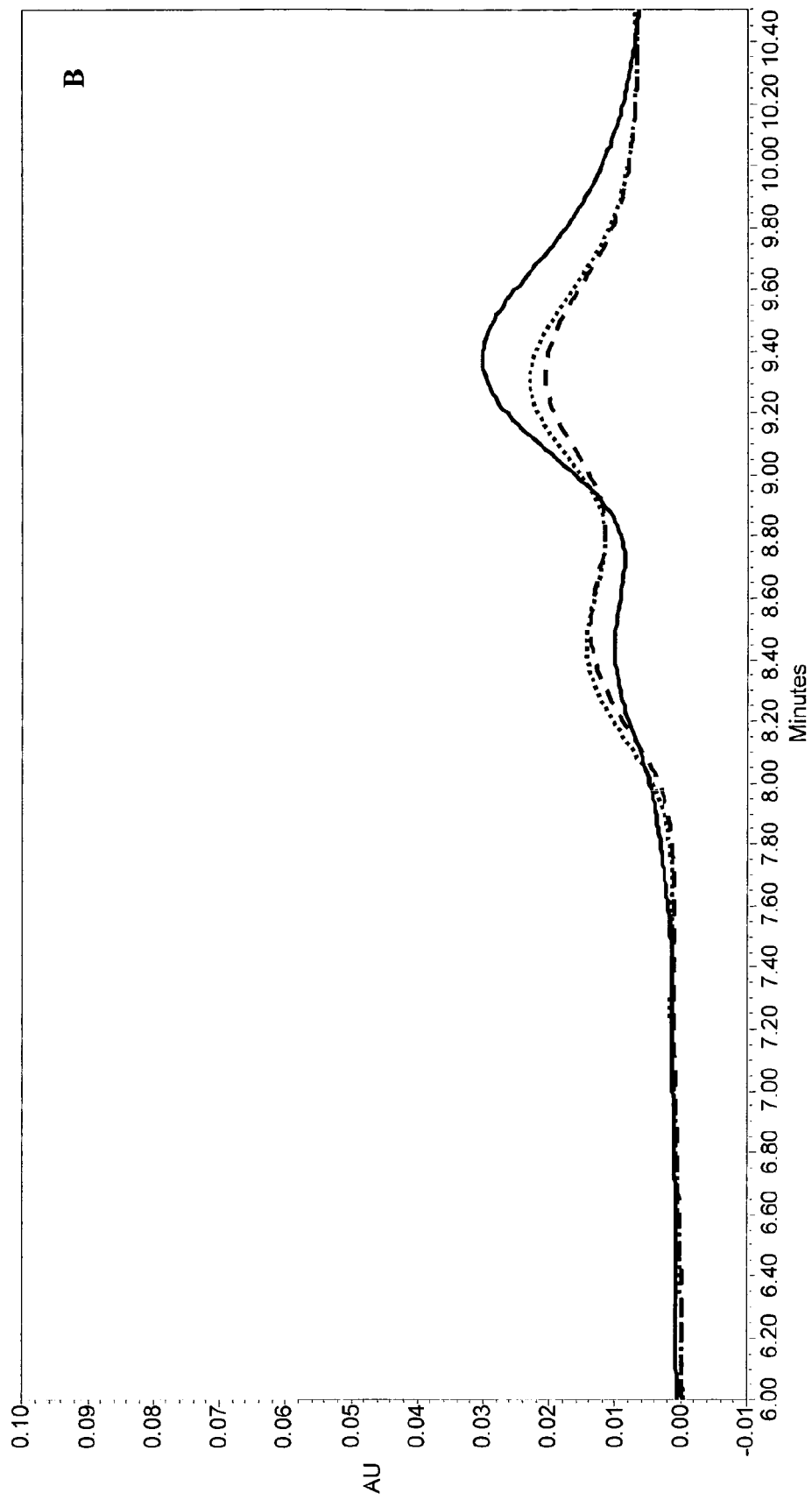
Figure 1 – Cont.

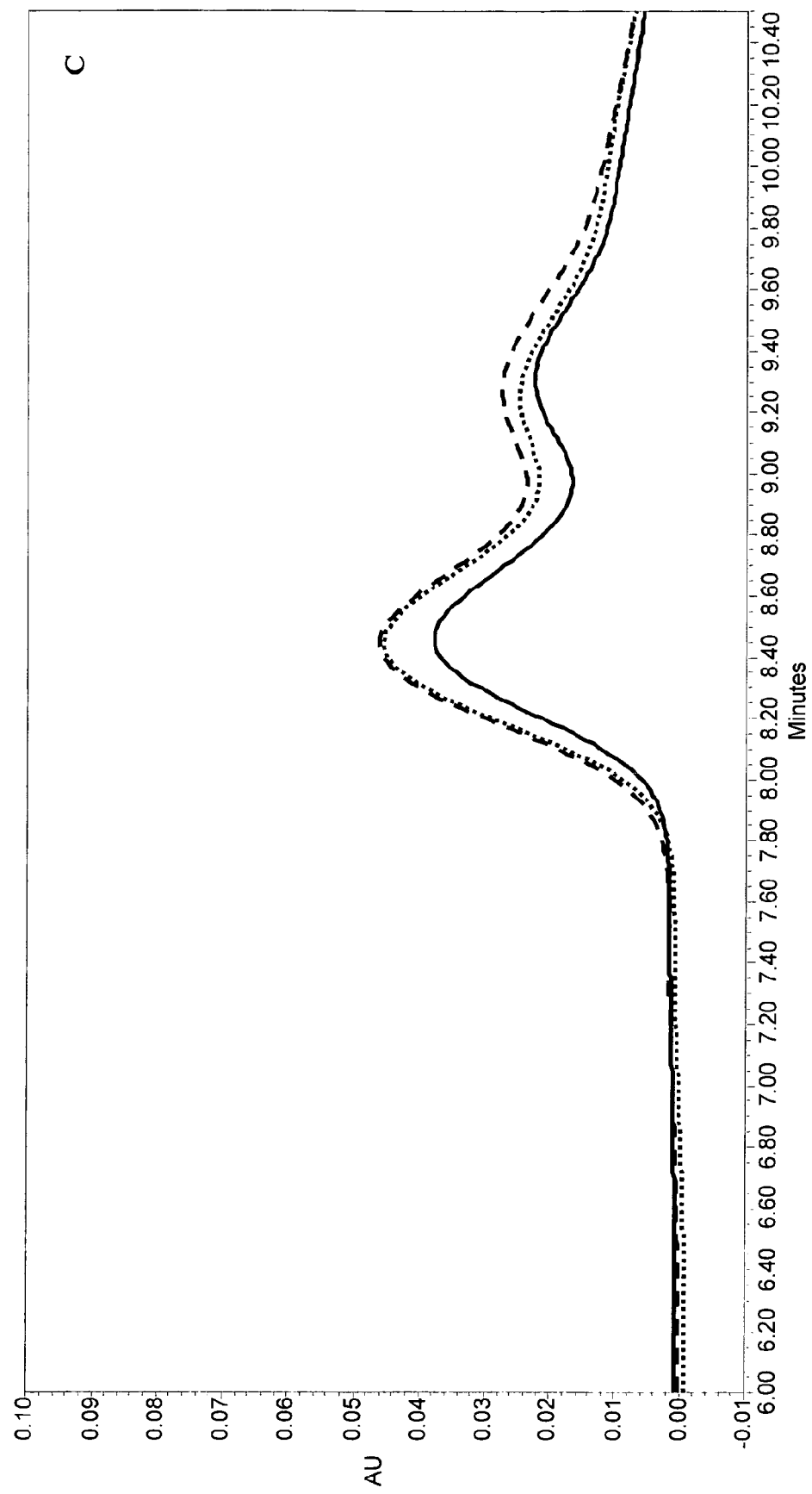
Figure 1 – Cont.

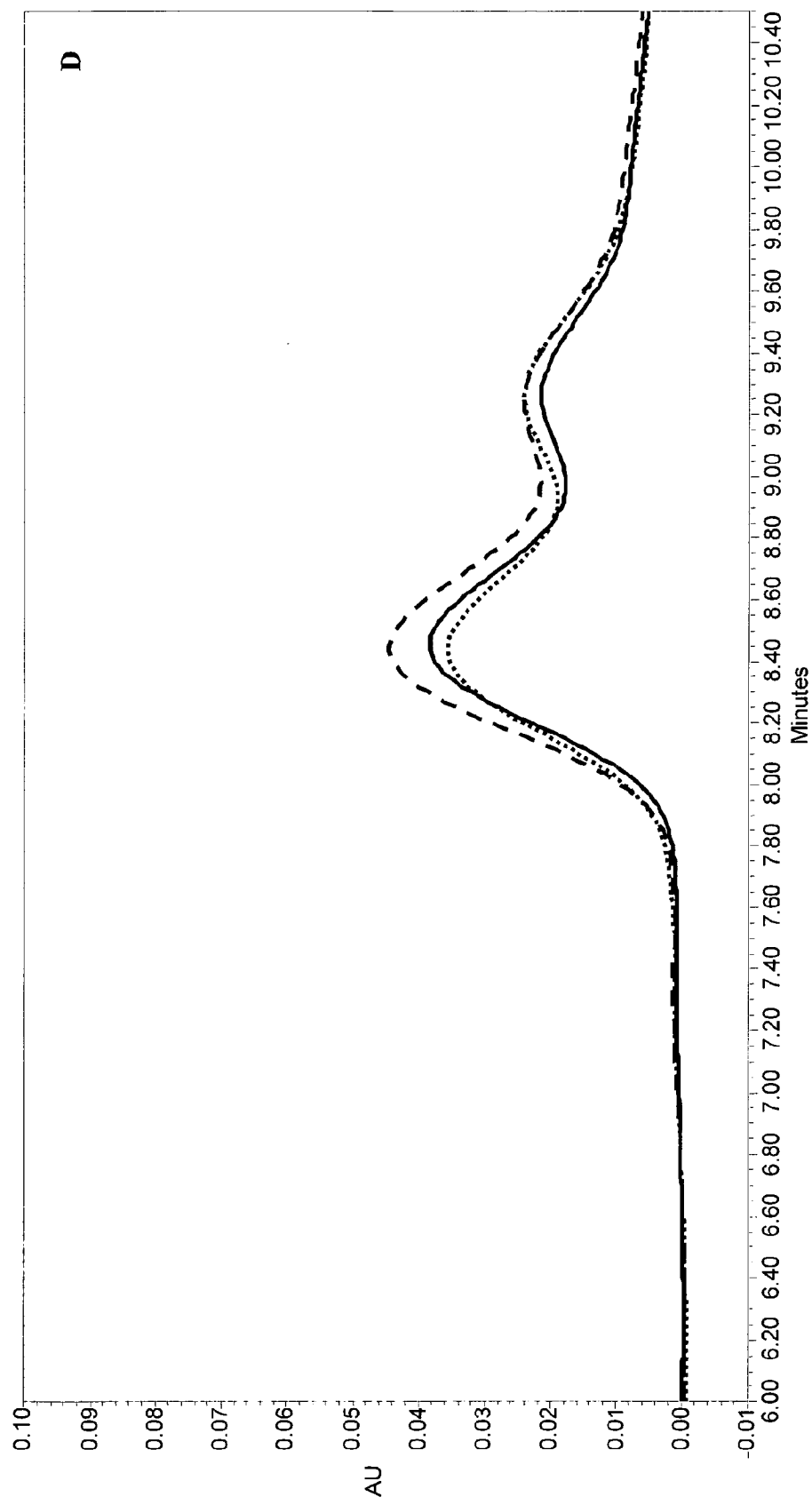
Figure 1 – Cont.

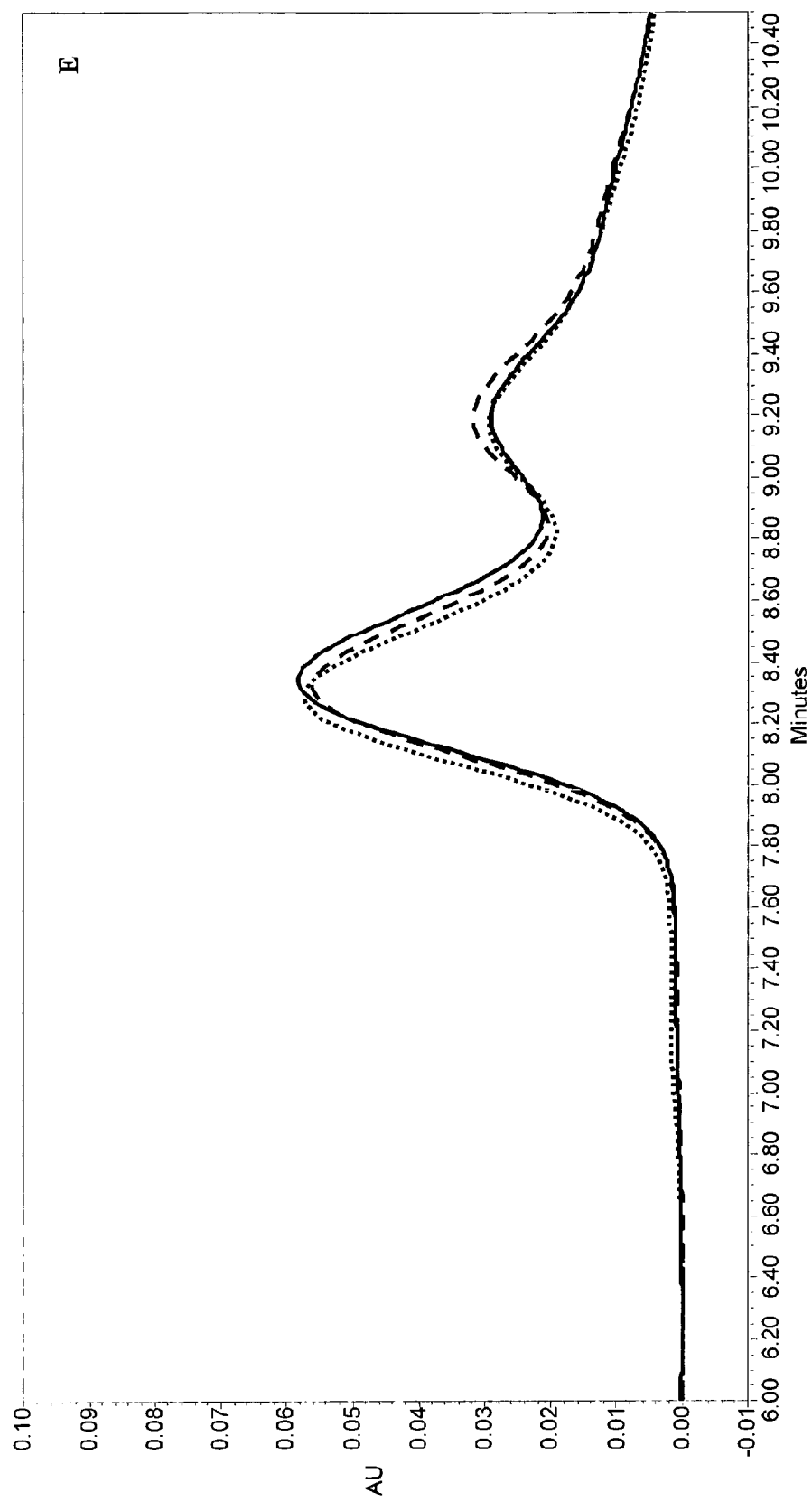
Figure 1 – Cont.

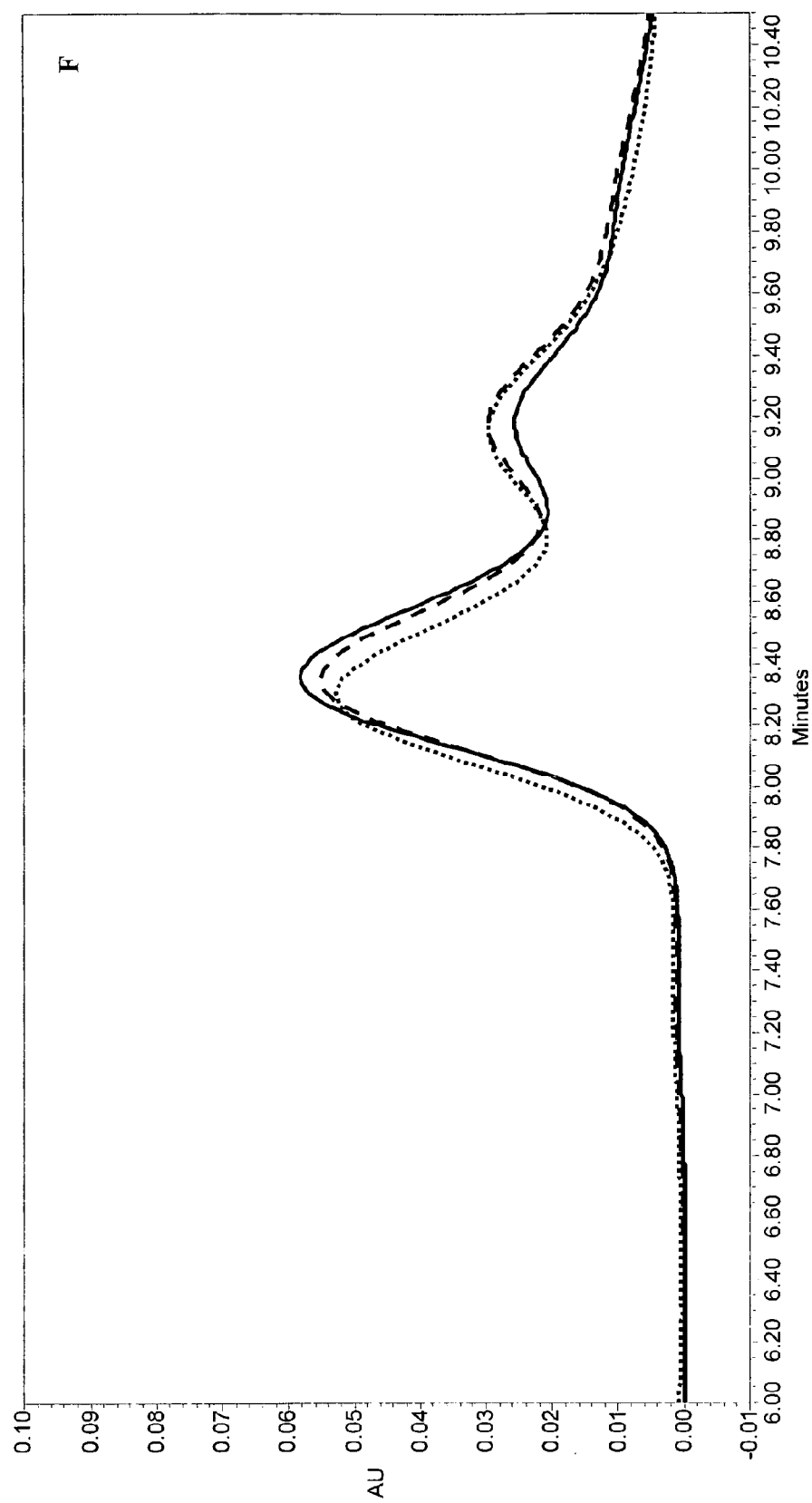
Figure 1 – Cont.

LH LIQUID FORMULATIONS

CROSS-REFERENCE TO RELATED APPLICATIONS

This application is a U.S. National Stage of International Application No. PCT/EP2008/064679 filed Oct. 29, 2008, which claims priority to EP application No. 07119832.9 filed Nov. 1, 2007 and claims the benefit of U.S. application Ser. No. 61/004,481 filed Nov. 28, 2007, which is incorporated herein by reference.

FIELD OF INVENTION

The invention relates to the field of liquid pharmaceutical formulations of luteinizing hormone (LH) as well as to methods of producing such formulations.

BACKGROUND OF THE INVENTION

Luteinizing hormone (LH), follicle-stimulating hormone (FSH) and chorionic gonadotropin (CG) are injectable proteins falling into the class of gonadotropins. LH, FSH and CG are used alone and in combination in the treatment of infertility and reproductive disorders in both female and male patients.

In nature, FSH and LH are produced by the pituitary gland. For pharmaceutical use, FSH and LH and their variants may be produced recombinantly (rFSH and rLH), or they may be produced from the urine of postmenopausal women (uFSH and uLH).

FSH is used in female patients in ovulation induction (OI) and in controlled ovarian hyperstimulation (COH) for assisted reproductive technologies (ART). In a typical treatment regimen for ovulation induction, a patient is administered daily injections of FSH or an FSH variant (about 75 to 300 IU FSH/day) for a period of from about 6 to about 12 days. In a typical treatment regimen for controlled ovarian hyperstimulation, a patient is administered daily injections of FSH or an FSH variant (about 150-600 IU FSH/day) for a period of from about 6 to about 12 days.

FSH is also used to induce spermatogenesis in men suffering from oligospermia. A regimen using 150 IU FSH 3 times weekly in combination with 2,500 IU hCG twice weekly has been successful in achieving an improvement in sperm count in men suffering from hypogonadotrophic hypogonadism (Burgues et al., 1997).

LH is used in female patients in combination with FSH in OI and in COH, particularly in those patients having very low endogenous LH levels or resistance to LH, such as women suffering from hypogonadotrophic hypogonadism (HH, WHO group I) or older patients (i.e. 35 years or older), and patients in which embryo implantation or early miscarriage is a problem. LH in combination with FSH has traditionally been available in a preparation called human menopausal gonadotropins (hMG) extracted from the urine of postmenopausal women. hMG has a 1:1 ratio of FSH:LH activity.

CG acts at the same receptor as LH and elicits the same responses. CG has a longer circulation half-life than LH and is therefore commonly used as a long-acting source of LH-activity. CG is used in OI and COH regimens to mimic the natural LH peak and trigger ovulation. An injection of human chorionic gonadotropin (hCG) is used to trigger ovulation at the end of stimulation with FSH or a mixture of FSH and LH. CG may also be used together with FSH during stimulation for OI and COH, in order to provide LH-activity during stimulation in patients in which LH-activity is desirable, such as those mentioned above.

FSH, LH and CG are members of the heterodimer, glycoprotein hormone family that also includes thyroid stimulating hormone (TSH). The members of this family are heterodimers, comprising an α- and a β-subunit. The subunits are held together by noncovalent interactions. The human FSH (hFSH) heterodimer consists of (i) a mature 92 amino acid glycoprotein alpha subunit, which also is common to the other human family members (i.e., chorionic gonadotropin ("CG"), luteinizing hormone ("LH") and thyroid stimulating hormone ("TSH"); and (ii) a mature 111 amino acid beta subunit that is unique to FSH (Shome et al., 1974 and 1988). The human LH heterodimer consists of (i) the mature 92 amino acid glycoprotein alpha subunit; and (ii) a mature 112 amino acid beta subunit that is unique to LH (Keutmann et al., 1979; Talmadge et al., 1984; Fiddes & Talmadge, 1984). The alpha and beta subunits of the glycoproteins may be prone to dissociate in formulations, due to interaction with a preservative, surfactant and other excipients. Dissociation of the subunits leads to loss of biological activity (Reichert & Ramsey, 1975).

FSH is formulated for intramuscular (IM) or subcutaneous (SC) injection. FSH is supplied in lyophilised (solid) form in vials or ampoules of 75 IU/vial and 150 IU/vial with a shelf life of about two years when stored at 2-25° C. A solution for injection is formed by reconstituting the lyophilised product with water for injection (WFI). For ovulation induction or controlled ovarian hyperstimulation, daily injections with starting doses of 75 IU to 600 IU are recommended for up to about ten days. Depending on the patient's response, up to three cycles of treatment with increasing doses of FSH can be used. With lyophilised formulations, the patient is required to reconstitute a new vial of lyophilised material with diluent and administer it immediately after reconstitution on a daily basis [Package insert N1700101A, published in February 1996, for Fertinex™ (urofollitropin for injection, purified) for subcutaneous injection, by Serono Laboratories, Inc., Randolph, Mass.].

FSH has also been formulated in both single-dose and multidose liquid formats, in vials, or ampoules. Single dose formats must remain stable and active in storage prior to use.

Multidose formats must not only remain stable and active in storage prior to use, but must also remain stable, active and relatively free of bacteria over the multiple day administration period, after the seal of the ampoule has been compromised. For this reason, multidose formats often contain a bacteriostatic agent.

LH is formulated for intramuscular (IM) or subcutaneous (SC) injection. LH is supplied in lyophilised (solid) form in vials or ampoules of 75 IU/vial with a shelf life of about two years when stored at 2-25° C. A solution for injection is formed by reconstituting the lyophilised product with water for injection (WFI). For ovulation induction or controlled ovarian hyperstimulation, in conjunction with FSH, daily injections with starting doses of 75 IU to 600 IU LH are recommended for up to about ten days.

EP 0 618 808 (Applied Research Systems ARS Holding N.V.) discloses a pharmaceutical composition comprising a solid intimate mixture of gonadotropin and a stabilising amount of sucrose alone or in combination with glycine.

EP 0 814 841 (Applied Research Systems ARS Holding N.V.) discloses a stable, liquid pharmaceutical composition comprising recombinant human chorionic gonadotropin (hCG) and a stabilizing amount of mannitol.

WO 2004/087213 (Ares Trading S.A.) discloses a liquid and a freeze-dried pharmaceutical composition comprising follicle-stimulating hormone (FSH) or a variant thereof and/or luteinizing hormone (LH) or a variant thereof as well as a surfactant selected from Pluronic® F77, Pluronic F87, Pluronic F88 and Pluronic F68.

WO 2004/112826 (Ares Trading S.A.) discloses a freeze-dried formulation comprising follicle-stimulating hormone (FSH) or a variant thereof and luteinizing hormone (LH) or a variant thereof as well as a surfactant selected from a polysorbate including TWEEN® 20, TWEEN® 40 and TWEEN® 80.

WO 00/04913 (Eli Lilly and Co.) discloses a formulation comprising FSH or an FSH variant, containing an alpha and beta subunit, and a preservative selected from the group consisting of phenol, m-cresol, p-cresol, o-cresol, chlorocresol, benzyl alcohol, alkylparaben (methyl, ethyl, propyl, butyl and the like), benzalkonium chloride, benzethonium chloride, sodium dehydroacetate and thimerosal, or mixtures thereof in an aqueous diluent.

WO 2004/105788 (Ferring B.V.) discloses a pharmaceutical composition consisting of FSH and hCG in at least one pharmaceutically acceptable carrier.

EP 0 448 146 (AKZO N.V.) discloses a stabilized gonadotropin-containing lyophilisate comprising a gonadotropin and a stabilizing amount of a dicarboxylic acid salt.

EP 0 853 945 (Akzo Nobel N.V.) discloses a liquid gonadotropin-containing formulation characterised in that the formulation comprises a gonadotropin and stabilising amounts of a polycarboxylic acid or a salt thereof and of a thioether compound.

There remains a need for stable liquid formulations of LH or a LH variant either for single-dose or multidose administration.

SUMMARY OF THE INVENTION

It is an object of the invention to provide liquid formulations of LH or LH variant, methods for their preparation, and methods for their pharmaceutical or veterinary use in the treatment of fertility disorders.

In a first aspect, the invention provides a liquid formulation of LH or an LH variant comprising a purified preparation of LH or LH variant, and a stabilizing amount of arginine or salts thereof and/or lysine or salts thereof.

In a second aspect, the invention provides a method for the preparation of a liquid formulation of LH or LH variant comprising the steps of a) forming a solution of LH or LH variant, and b) adding to said solution a stabilizing amount of arginine or salts thereof and/or lysine or salts thereof.

In a third aspect, the invention provides a presentation form of a liquid formulation of LH or LH variant comprising the liquid formulation according to the invention, hermetically sealed under sterile conditions in a container suitable for storage prior to use. The container may be an ampoule, a vial, a syringe, or a cartridge.

In a fourth aspect, the invention provides an article of manufacture for human pharmaceutical use, comprising packaging material and a container comprising the liquid formulation of LH or LH variant according to the invention and a bacteriostatic agent, wherein said packaging material comprises a label which indicates that such formulation may be held over a period of twenty-eight days or greater after the first use.

It is a further object of the invention to provide the use of a liquid formulation of LH or LH variant according to the invention in combination with liquid formulations of FSH or FSH variant.

DETAILED DESCRIPTION OF THE INVENTION

Figure 1:
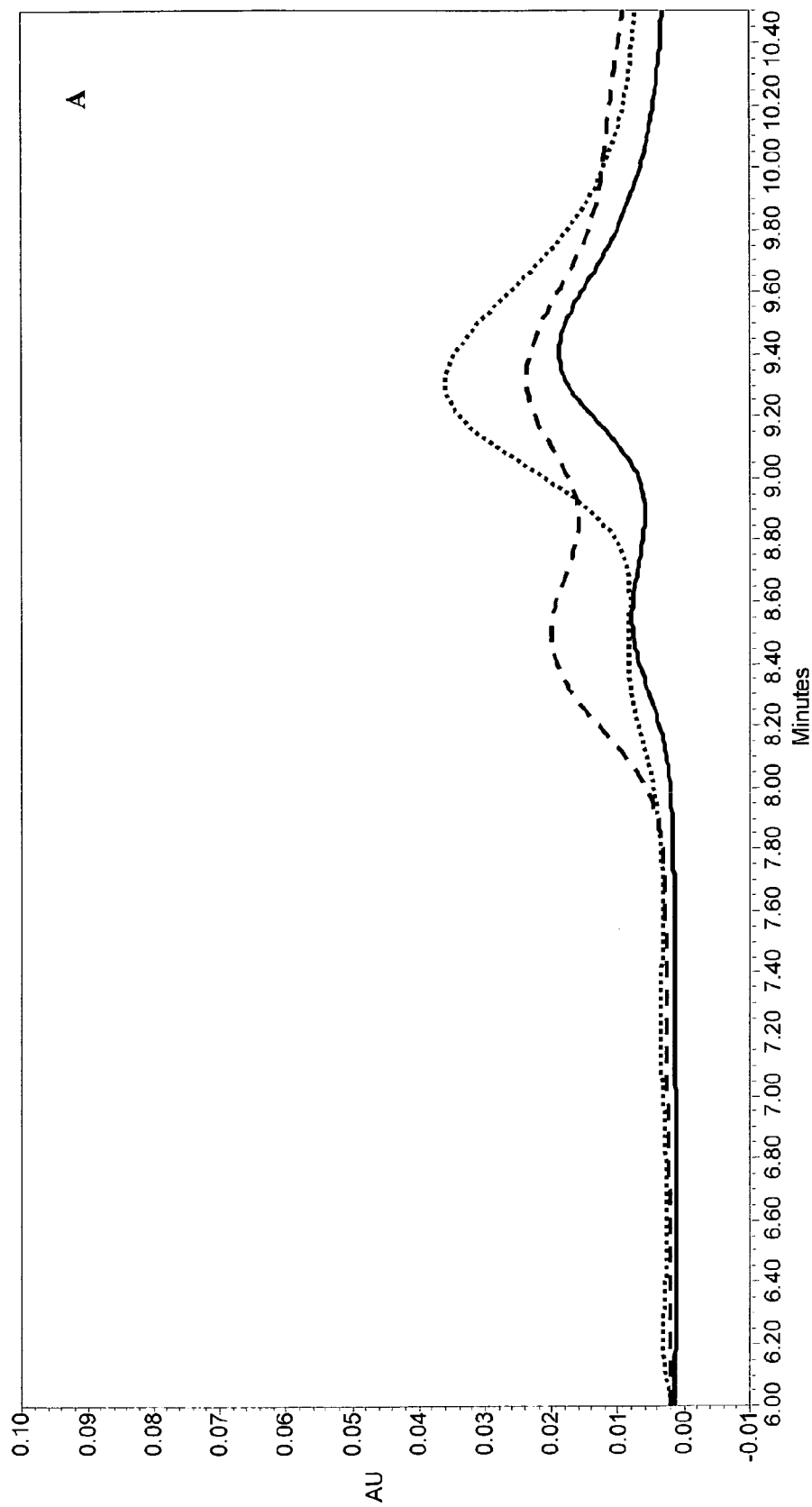
FIG. 1 shows the comparison of chromatographic profiles (by SE-HPLC) of r-hLH formulations with different concentrations (6, 12 and 24 µg/ml of r-hLH), containers (syringe and cartridge) and filling volumes (0.25, 0.5 and 1 ml). These formulations, in addition to r-hLH, contain phosphate buffer, saccharose, TWEEN® 20 polysorbate, methionine, benzyl alcohol, benzalkonium chloride and water for injection. The grey lines correspond to a filling volume of 0.25 ml; the dashed lines correspond to a filling volume of 0.5 ml; and the black lines to a filling volume of 1 ml. (A) 6 µg/ml r-hLH formulation in syringe. (B) 6 µg/ml r-hLH formulation in cartridge. (C) 12 µg/ml r-hLH formulation in syringe. (D) 12 µg/ml r-hLH formulation in cartridge. (E) 24 µg/ml r-hLH formulation in syringe. (F) 24 µg/ml r-hLH formulation in cartridge. The peaks at a retention time of 8.5 minutes correspond to the intact heterodimers (alpha+beta subunits linked through a non-covalent bound), while peaks at higher retention time (about 9.5 minutes) correspond to the free-subunits. AU: absorbance unit.

The liquid LH formulations of the present invention have improved or more suitable properties or stability, and are useful for infertility treatment in women and/or men.

In a preferred embodiment the liquid formulations of the invention are for subcutaneous and/or intramuscular injection.

The suitable properties or stability of the LH or LH variant liquid formulations according to the invention are obtained by preventing or reducing loss of activity or stability, or by improving any aspect of the effectiveness or desirability of administration, e.g., by at least one of mode, frequency, dosage, comfort, ease of use, and the like.

Luteinising hormone, or LH, as used herein refers to the LH produced as a full-length mature protein, which includes, but is not limited to human LH or "hLH", whether produced recombinantly or isolated from human sources, such as the urine of postmenopausal women.

The expression "LH variant" is meant to encompass those molecules differing in amino acid sequence, glycosylation pattern or in inter-subunit linkage from human LH but exhibiting LH-activity.

The term "activity" in relation to LH, refers to the ability of an LH formulation or a mixed formulation, to elicit biological responses associated with LH, such as seminal vesicle weight gain method (Van Hell et al., 1964). Biological activity of LH is evaluated with respect to an accepted standard for LH.

Measure of activity is expressed in International Units per milliliter of solution (IU/ml) or in Mega International Units per milliliter of solution (MIU/ml). (1 MIU/ml=1,000,000 IU/ml). An International Unit is calculated as described in the Research Reference Reagent Note No. 35, published by the National Institute of Health, Bethesda, Md.

LH or LH variant can be produced by any suitable method, such as recombinantly, by isolation or purification from natural sources as may be the case, or by chemical synthesis, or any combination thereof.

The use of the term "recombinant" refers to preparations of LH or a LH variant that are produced through the use of recombinant DNA technology (see for example WO 85/01958). One example of a method of expressing LH using recombinant technology is by transfection of eukaryotic cells with the DNA sequences encoding an alpha and beta subunit of LH, whether provided on one vector or on two vectors with each subunit having a separate promoter, as described in European patent nos. EP 0 211 894 and EP 0 487 512.

Another example of the use of recombinant technology to produce LH is by the use of homologous recombination to insert a heterologous regulatory segment in operative connection to endogenous sequences encoding the subunits of LH, as described in European patent no. EP 0 505 500 (Applied Research Systems ARS Holding Nev.).

Follicle stimulating hormone, or FSH, as used herein refers to the FSH produced as a full-length mature protein which includes, but is not limited to human FSH or "hFSH", whether produced recombinantly or isolated from human sources, such as the urine of postmenopausal women.

The expression "FSH variant" is meant to encompass those molecules differing in amino acid sequence, glycosylation pattern or in inter-subunit linkage from human FSH but exhibiting FSH-activity.

The term "activity" in relation to FSH, refers to the ability of an FSH formulation or a mixed formulation, to elicit biological responses associated with FSH, such as ovarian weight gain in the Steelman-Pohley assay (Steelman et al., 1953), or follicular growth in a female patient. Follicular growth in a female patient can be evaluated by ultrasound, for example, in terms of the number of follicles having a mean diameter of at or about 16 mm on day 8 of stimulation. Biological activity is evaluated with respect to an accepted standard for FSH.

Examples of FSH variant include CTP-FSH, a long-acting modified recombinant FSH, consisting of the wild type α-subunit and a hybrid β-subunit in which the carboxy terminal peptide of hCG has been fused to the C-terminal of the β-subunit of FSH, as described in LaPolt et al. (1992) or in Klein et al. (2003). Also included is single chain CTP-FSH, a single chain molecule, consisting of the following sequences (from N-terminal to C-terminal):

| βFSH | βhCG-CTP(113-145) | αFSH |
--- wherein βFSH signifies the β-subunit of FSH, βhCG CTP (113-145) signifies the carboxy terminal peptide of hCG and αFSH signifies the α-subunit of FSH, as described by Klein et al. (2002).

Other examples of FSH variants include FSH molecules having additional glycosylation sites incorporated in the α- and/or β-subunit, as disclosed in WO 01/58493 (Maxygen), particularly as disclosed in claims 10 and 11 of WO 01/58493, and FSH molecules with intersubunit S—S bonds, as disclosed in WO 98/58957.

FSH or FSH variant can be produced by any suitable method, such as recombinantly, by isolation or purification from natural sources as may be the case, or by chemical synthesis, or any combination thereof.

The FSH or FSH variant used in accordance with the present invention may be produced not only by recombinant means, including from mammalian cells, but also may be purified from other biological sources, such as from urinary sources. Acceptable methodologies include those described in Hakola et al. (1997), Keene et al. (1989), Cerpa-Poljak et al. (1993), Dias et al. (1994); Flack et al. (1994), Valove et al. (1994), U.S. Pat. No. 3,119,740 and U.S. Pat. No. 5,767,067.

The term "administer" or "administering" means to introduce a formulation of the present invention into the body of a patient in need thereof to treat a disease or condition.

The term "patient" means a mammal that is treated for a disease or condition. Patients are of, but not limited to, the following origin, human, ovine, porcine, equine, bovine, rabbit and the like.

The term "aqueous diluent" refers to a liquid solvent that contains water. Aqueous solvent systems may be consist solely of water, or may consist of water plus one or more miscible solvents, and may contain dissolved solutes such as sugars, buffers, salts or other excipients. The more commonly used non-aqueous solvents are the short-chain organic alcohols, such as, methanol, ethanol, propanol, short-chain ketones, such as acetone, and poly alcohols, such as glycerol.

An "isotonicity agent" is a compound that is physiologically tolerated and imparts a suitable tonicity to a formulation to prevent the net flow of water across cell membranes that are in contact with the formulation.

Compounds such as glycerin, are commonly used for such purposes at known concentrations. Other suitable isotonicity agents include, but are not limited to, amino acids or proteins (e.g., glycine or albumin), salts (e.g., sodium chloride), and sugars (e.g., dextrose, sucrose and lactose).

The term "bacteriostatic" or "bacteriostatic agent" refers to a compound or compositions added to a formulation to act as an anti-bacterial agent. A preserved LH or LH variant containing formulation of the present invention preferably meets statutory or regulatory guidelines for preservative effectiveness to be a commercially viable multi-use product, preferably in humans.

Examples of bacteriostatics include phenol, m-cresol, p-cresol, o-cresol, chlorocresol, benzyl alcohol, alkylparaben (methyl, ethyl, propyl, butyl and the like), benzalkonium chloride, benzethonium chloride, sodium dehydroacetate and thimerosal.

The term "buffer" or "physiologically-acceptable buffer" refers to solutions of compounds that are known to be safe for pharmaceutical or veterinary use in formulations and that have the effect of maintaining or controlling the pH of the formulation in the pH range desired for the formulation. Acceptable buffers for controlling pH at a moderately acidic pH to a moderately basic pH include, but are not limited to, such compounds as phosphate, acetate, citrate, arginine, TRIS, and histidine. "TRIS" refers to 2-amino-2-hydroxymethyl-1,3,-propanediol, and to any pharmacologically acceptable salt thereof. Preferable buffers are phosphate buffers with saline or an acceptable salt.

The term "phosphate buffer" refers to solutions containing phosphoric acid or salts thereof, adjusted to a desired pH. Generally phosphate buffers are prepared from phosphoric acid, or a salt of phosphoric acid, including but not limited to sodium and potassium salts. Several salts of phosphoric acid are known in the art, such as sodium and potassium monobasic, dibasic, and tribasic salts of the acid. Salts of phosphoric acid are also known to occur as hydrates of the occurring salt. Phosphate buffers may cover a range of pHs, such as from about pH 4 to about pH 10, and preferred ranges from about pH 5 to about pH 9, and a most preferred range of at or about 7.5 to at or about 8.5, most preferably at or about pH 8.0.

The term "vial" or "container" refers broadly to a reservoir suitable for retaining LH and diluent in a contained sterile state. Examples of a vial as used herein include ampoules, cartridges, blister packages, or other such reservoir suitable for delivery of the LH to the patient via syringe, pump (including osmotic), catheter, transdermal patch, pulmonary or transmucosal spray. Vials suitable for packaging products for parenteral, pulmonary, transmucosal, or transdermal administration are well known and recognized in the art.

The term "stability" refers to the physical, chemical, and conformational stability of LH in the formulations of the present invention (including maintenance of biological activity). Instability of a protein formulation may be caused by chemical degradation or aggregation of the protein molecules to form higher order polymers, by dissociation of the heterodimers into monomers, deglycosylation, modification of glycosylation, oxidation (particularly of the α-subunit) or any other structural modification that reduces at least one biological activity of an LH polypeptide included in the present invention.

A "stable" solution or formulation, is one wherein the degree of degradation, modification, aggregation, loss of biological activity and the like, of proteins therein is acceptably controlled, and does not increase unacceptably with time. Preferably the formulation retains at least at or about 80% of the labelled LH activity over a period of 6 months at a temperature of at or about 1-10° C., more preferably at or about 2-8° C., more preferably at or about 4-5° C. LH activity can be measured using the seminal vesicle weight gain bioassay[6].

The term "treating" refers to the administration, follow up, management and/or care of a patient for which LH administration is desirable for the purpose of follicle or testicular stimulation or any other physiological response regulated by LH. Treating can thus include, but is not limited to, the administration of LH for the induction or improvement of sperm quality, stimulation of testosterone release in the male, or follicular development or for ovulation induction in the female.

The expression "multidose use" is intended to include the use of a single ampoule, vial, or cartridge of an LH formulation for more than one injection, for example 2, 3, 4, 5, 6 or more injections. The injections are preferably made over a period of at least at or about 12 hours, 24 hours, 48 hours, etc., preferably up to a period of at or about 28 days.

The injections may be spaced in time, for example, by a period of 6, 12, 24, 48 or 72 hours.

A "salt" of a protein is an acid or base addition salt. Such salts are preferably formed between any one or more of the charged groups in the protein and any one or more physiologically acceptable, non-toxic cations or anions. Organic and inorganic salts include, for example, those prepared from acids such as hydrochloric, sulphuric, sulfonic, tartaric, fumaric, hydrobromic, glycolic, citric, maleic, phosphoric, succinic, acetic, nitric, benzoic, ascorbic, p-toluenesulfonic, benzenesulfonic, naphthalenesulfonic, propionic, carbonic, and the like, or for example, ammonium, sodium, potassium, calcium, or magnesium.

It has been found that an amino acid selected from the group of arginine, lysine or a mixture or a salt thereof is a suitable stabilizing agent for preparing a stable liquid formulation comprising LH. Therefore, the first aspect of the invention relates to a liquid gonadotropin formulation containing luteinizing hormone (LH) or a variant thereof characterized in that said formulation comprises a stabilizing amount of arginine or salts thereof and/or lysine or salts thereof.

The stabilizing amount of arginine or salts thereof and/or lysine or salts thereof present in the liquid formulation is at a concentration of at or about 10 to at or about 150 mg/ml of the total formulation, more preferably at or about 20 to at or about 60 mg/ml.

Preferably the concentration of arginine or salts thereof is at or about 10 mg/ml to at or about 50 mg/ml, more preferably at or about 20 mg/ml to at or about 40 mg/ml, more particularly preferably at or about 25 mg/ml to at or about 35 mg/ml, most preferably at or about 31.5 mg/ml.

Preferably the concentration of lysine or salts thereof is at or about 10 mg/ml to at or about 50 mg/ml, more preferably at or about 20 mg/ml to at or about 40 mg/ml, more particularly preferably at or about 25 mg/ml to at or about 35 mg/ml, most preferably at or about 28.5 mg/ml.

The luteinizing hormone (LH) within the liquid formulation is preferably present at a concentration of at or about 1 to at or about 50 µg/ml of the total formulation. In one embodiment, the luteinizing hormone (LH) is present at a concentration of at or about 1 to 15 µg/ml of the total formulation, in particular when intended for single use.

In a further embodiment, the luteinizing hormone (LH) is present at a concentration of at or about 15 to 30 µg/ml of the total formulation, in particular when intended for multiple use (multidose).

The LH concentration in the formulation is preferably at or about 20 IU/ml to at or about 2,000 IU/ml, more preferably at or about 50 to at or about 1,000 IU/ml, more particularly preferably at or about 100 IU/ml to at or about 600 IU/ml.

Preferably the LH is produced recombinantly, particularly preferably it is produced in Chinese hamster ovary (CHO) cells transfected with an expression vector or vectors comprising DNA coding for the human glycoprotein alpha-subunit and the beta-subunit of LH. DNA encoding the alpha and beta-subunits may be present on the same or different vectors.

Recombinant LH has several advantages over its urinary counterparts. Culture and isolation techniques using recombinant cells permit consistency between batches. In contrast, urinary LH varies greatly from batch to batch in such characteristics as purity, glycosylation pattern, sialylation and oxidation of the subunits. Due to greater batch-to-batch consistency and purity of recombinant LH, the hormones can be readily identified and quantified using techniques such as isoelectric focusing (IEF). The ease with which recombinant LH can be identified and quantified permits the filling of vials by mass of hormone (fill-by-mass) rather than filling by bioassay.

Preferably the liquid formulations of the present invention have a buffer, preferably a phosphate buffer, with preferred counterions being sodium or potassium ions. Phosphate saline buffers are well known in the art, such as Dulbecco's Phosphate buffered saline. Buffer concentrations in total solution can vary between at or about 1 mM, 5 mM, 9.5 mM, 10 mM, 50 mM, 100 mM, 150 mM, 200 mM, 250 mM, and 500 mM. Preferably the buffer concentration is at or about 10 mM. Particularly preferred is a buffer 10 mM in phosphate ions with a pH of at or about 8.0.

Preferably the buffer is adjusted in such a way that the liquid formulations of the present invention have a pH between at or about 7.0 and at or about 9.0, more preferably at or about 7.5 to at or about 8.5, including about pH 7.8, pH 8.0, and 8.2. The invention is directed to liquid formulations of LH or LH variant that may be single dose or multidose.

Those liquid LH formulations of the invention that are intended for multidose use comprise a bacteriostatic agent, such as phenol, m-cresol, p-cresol, o-cresol, chlorocresol, benzyl alcohol, alkylparaben (methyl, ethyl, propyl, butyl and the like), benzalkonium chloride, benzethonium chloride, sodium dehydroacetate and thimerosal. Preferred are benzyl alcohol, phenol, and combination of benzyl alcohol and benzalkonium chloride. The bacteriostatic agent is used in an amount that will yield a concentration that is effective to maintain the formulation essentially bacteria free (suitable for injection) over the multidose injection period, which may be at or about 12 or 24 hours to at or about 12 or 14 days, preferably at or about 6 to at or about 28 days.

The bacteriostatic agent is preferably present in a concentration of at or about 0.005 to at or about 15 mg/ml, more preferably at or about 0.01 to at or about 12 mg/ml. The bacteriostatic agent is preferably present in a concentration of at or about 0.1% (mass bacteriostatic/mass of solvent) to at or about 2.0%, more preferably at or about 0.2% to at or about 1.0%.

In the case of benzyl alcohol, particularly preferred is a concentration of 0.9% or 1.2%. In the case of phenol, particularly preferred is at or about 0.5%. In the case of combination of benzyl alcohol and benzalkonium chloride, particularly preferred is a concentration of 0.3% and 0.001%, respectively.

Preferably the formulations of the invention contain an antioxidant, such as methionine, sodium bisulfite, salts of ethylenediaminetetraacetic acid (EDTA), butylated hydroxytoluene (BHT), and butylated hydroxy anisole (BHA). Most preferred is methionine. The antioxidant prevents oxidation of LH (particularly the α-subunit).

The antioxidant, e.g. methionine is preferably present at a concentration of at or about 0.01 to at or about 5.0 mg/ml, more preferably at or about 0.05 to at or about 0.5 mg/ml.

Preferably the formulations of the invention contain a surfactant. Preferably the surfactant is selected from the group of polysorbates, in particular TWEEN® 20 (polyoxyethylene (20) sorbitan monolaurate), TWEEN® 40 (polyoxyethylene (20) sorbitan monopalmitate) and TWEEN® 80 (polyoxyethylene (20) sorbitan monooleate). Most preferred is TWEEN® 20, preferably at a concentration of at or about 0.01 to at or about 10 mg/ml.

In a preferred embodiment the formulations of the invention comprise at least 25 μg/ml of r-hLH, 1.65 mg/ml of Na2HPO4 2H2O, 0.104 mg/ml of NaH2PO4 H2O, 31.5 mg/ml of arginine monohydrochloride, 0.05 mg/ml of Tween TWEEN® 20 polysorbate, 0.5 mg/ml of methionine and 5 mg/ml of phenol.

In another preferred embodiment the formulations of the invention comprise at least 25 g/ml of r-hLH, 1.65 mg/ml of Na2HPO4 2H2O, 0.104 mg/ml of NaH2PO4 H2O, 28.5 mg/ml of lysine monohydrochloride, 0.05 mg/ml of Tween TWEEN® 20 polysorbate, 0.5 mg/ml of methionine and 12 mg/ml of benzylalcohol.

In another preferred embodiment the formulations of the invention comprise at least 25 g/ml of r-hLH, 1.65 mg/ml of Na2HPO4 2H2O, 0.104 mg/ml of NaH2PO4 H2O, 28.5 mg/ml of lysine monohydrochloride, 0.05 mg/ml of Tween TWEEN® 20 polysorbate, 0.5 mg/ml of methionine 3 mg/ml of benzylalcohol and 0.01 mg/ml of benzalkonium chloride.

In a preferred embodiment, the invention provides a liquid pharmaceutical composition, for multidose use, comprising LH or LH variant, a stabilizing agent selected from the group of arginine, lysine or a mixture or a salt thereof, and a bacteriostatic agent selected from benzyl alcohol, phenol, and a combination of benzyl alcohol and benzalkonium chloride.

In a further preferred embodiment, the invention provides a method for manufacturing a liquid pharmaceutical composition, for multidose use, comprising forming an aqueous solution of LH or LH variant, a stabilizing agent selected from the group of arginine, lysine or a mixture or a salt thereof, and a bacteriostatic agent selected from benzyl alcohol, phenol, and a combination of benzyl alcohol and benzalkonium chloride, and WFI (water for injection).

In yet another preferred embodiment, the invention provides a method for manufacturing a packaged pharmaceutical composition comprising dispensing a solution comprising LH or LH variant, a stabilizing agent selected from the group of arginine, lysine or a mixture or a salt thereof, and a bacteriostatic agent selected from benzyl alcohol, phenol, and a combination of benzyl alcohol and benzalkonium chloride.

In yet another preferred embodiment, the invention provides an article of manufacture for human pharmaceutical use, comprising a vial comprising a solution of LH or LH variant, a stabilizing agent selected from the group of arginine, lysine or a mixture or a salt thereof, and a bacteriostatic agent selected from benzyl alcohol, phenol, and a combination of benzyl alcohol and benzalkonium chloride, and a label stating that such solution may be held over a period of at or about twenty-four hours or greater after the first use. Preferably the label states that the solution may be held up to at or about 12 or 14 days after the first use.

Before the first use, that is before the seal of the vial ampoule or cartridge has been broken, the formulations of the invention may be kept for at least at or about 6 months, 12 months or 24 months.

Under preferred storage conditions, before the first use, the formulations are kept away from bright light (preferably in the dark), at temperatures of at or about 2-8° C., more preferably at or about 4-5° C.

As noted above, the invention provides liquid formulations of LH or LH variant for single use and multidose use, containing a bacteriostatic. The formulations of the invention are suitable for pharmaceutical or veterinary use.

As noted above, in a preferred embodiment, the invention provides an article of manufacture, comprising packaging material and a vial comprising a solution of LH or LH variant, a stabilizing agent selected from the group of arginine, lysine or a mixture or a salt thereof, a bacteriostatic agent selected from benzyl alcohol, phenol, and a combination of benzyl alcohol and benzalkonium chloride, optionally with buffers and/or other excipients, in an aqueous diluent, wherein said packaging material comprises a label which indicates that such solution may be held over a period of twenty-four hours or greater after the first use.

Preferably the formulations of the invention retain at least at or about 80% of the LH activity at the time of packaging over a period of 24 months (before the first use). LH activity can be measured using the rat seminal vesicle weight gain bioassay[5].

The formulations of the present invention can be prepared by a process which comprises mixing LH or a variant thereof and a stabilizing amount of arginine or salts thereof and/or lysine or salts thereof, and optionally a bacteriostatic agent selected from benzyl alcohol, phenol, and a combination of benzyl alcohol and benzalkonium chloride as solids or dissolving LH or a variant thereof and a stabilizing amount of arginine or salts thereof and/or lysine or salts thereof, and optionally a bacteriostatic agent selected from benzyl alcohol, phenol, and a combination of benzyl alcohol and benzalkonium chloride in an aqueous diluent. Mixing the components and dissolving them in an aqueous diluent is carried out using conventional dissolution and mixing procedures. To prepare a suitable formulation, for example, a measured amount of LH or LH variant in buffered solution is combined with arginine or salts thereof and/or lysine or salts thereof and optionally a bacteriostatic selected from benzyl alcohol, phenol, and a combination of benzyl alcohol and benzalkonium chloride in a buffered solution in quantities sufficient to provide the protein, arginine or salts thereof and/or lysine or salts thereof and the optional bacteriostatic at the desired concentrations. The resulting solution is then dispensed into vials, ampoules or cartridges. Variations of this process would be recognized by one of ordinary skill in the art.

For example, the order the components are added, whether additional additives are used, the temperature and pH at which the formulation is prepared, are all factors that may be optimised for the concentration and means of administration used.

In a preferred embodiment, the formulations of the invention are made by preparing individual stock solutions of known concentration of all the components of the formulation (e.g. buffer sodium phosphate, arginine or salts thereof and/or lysine or salts thereof, TWEEN® 20 polysorbate, methionine, LH), and aliquoting volumetric amounts to form a "mother solution" of the same composition as the final formulation. The "mother solution" is preferably filtered through a Duropore® (Millipore) 0.22 micron PDF membrane, to remove microorganisms, and then aliquots are dispensed into individual containers, such as vials, ampoules or cartridges.

The formulations of the present invention can be used in combination with formulations comprising FSH or FSH variant (e.g. Gonal-F®).

The formulations of the present invention can be administered using recognized devices. Examples comprising these single vial systems include pen-injector devices for delivery of a solution such as EasyJect®, Gonal-F® Pen, Humaject®, NovoPen®, B-D®Pen, AutoPen®, and OptiPen®.

The products presently claimed include packaging material. The packaging material provides, in addition to the information required by the regulatory agencies, the conditions under which the product may be used. For the single vial, solution product, the label indicates that such solution may be stored after first use for a period of twenty-four hours or greater, preferably for up to 12 or 14 days. The presently claimed products are useful for human pharmaceutical product use.

The following examples are provided merely to further illustrate the preparation of the formulations and compositions of the invention. The scope of the invention shall not be construed as merely consisting of the following examples.

EXAMPLES

Materials

| Item | Manufacturer |
| --- | --- |
| r-hLH Bulk | Laboratoires Serono SA |
| L-Arginine monohydrochloride | Merck code 1.01544 |
| Benzalkonium chloride | Fluka code 12063 |
| Benzyl alcohol | Merck code 1.00987 |
| m-Cresol | Merck code 8.09691 |
| L-Glycine | Merck code 5.00190 |
| L-Lysine monohydrochloride | Merck code 1.05701 |
| Methionine | Merck code 1.05707 |
| Phenol | Merck code 1.00200 |
| Ortho-phosphoric Acid 85% (Ph Eur, BP, NF) | Merck code 1.00563 |
| Sodium hydroxide | Merck code 1.06498 |
| di-Sodium hydrogen phosphate dihydrate | Merck code 1.06580 |
| Sodium dihydrogen phosphate monohydrate | Merck code 1.06346 |
| Sodium sulphate anhydrous | Merck code 1.006649 |
| Sorbitol | Sigma code S-1876 |
| Saccharose | Merck code 1.07653 |
| Trehalose | Merck code 1.08216 |
| TWEEN ® 20 polysorbate | Merck code 8.22184 |
| Water | milliQ |

The following study evaluated the following parameters for a large number of formulations:
  Investigation on stabilizing and/or bacteriostatic agents
  Compatibility with FSH formulations
  Compatibility with primary packaging
  Stability profile after storage The formulations were liquid monodose and multidose formulations. The following six stabilizing agents were evaluated:
  L-Arginine monohydrochloride (ARG or arginine in the examples)
  L-Lysine monohydrochloride (LYS or lysine in the examples)
  Trehalose (TRE)
  L-Glycine (GLY or glycine in the examples)
  Saccharose (SAC)
  Sorbitol (SOR)

The following four bacteriostatic agents were evaluated for the multidose formulations:
  Benzyl alcohol (BA)
  m-Cresol (mCr)
  Phenol (Phe)
  Combination of benzyl alcohol and benzalkonium chloride (BACL)

Example 1

Investigation on Stabilizing Agents for Monodose Formulations

Six stabilizing agents (saccharose, arginine, glycine, lysine, sorbitol and trehalose) were tested to deliver stable monodose formulations. The tested formulations are summarized in Table 1.

TABLE 1

Composition of several r-hLH monodose formulations containing different stabilizing agents

| Components Amount/ml | SAC/250 | ARG/250 | GLY/250 | LYS/250 | SOR/250 | TRE/250 |
| --- | --- | --- | --- | --- | --- | --- |
| r-hLH bulk | 6 µg | 6 µg | 6 µg | 6 µg | 6 µg | 6 µg |
| $Na_2HPO_4$ $2H_2O$ | 1.65 mg | 1.65 mg | 1.65 mg | 1.65 mg | 1.65 mg | 1.65 mg |
| $NaH_2PO_4$ $H_2O$ | 0.104 mg | 0.104 mg | 0.104 mg | 0.104 mg | 0.104 mg | 0.104 mg |

TABLE 1-continued

Composition of several r-hLH monodose formulations containing different stabilizing agents

| Components Amount/ml | SAC/250 | ARG/250 | GLY/250 | LYS/250 | SOR/250 | TRE/250 |
|---|---|---|---|---|---|---|
| Methionine | 250 μg | 250 μg | 250 μg | 250 μg | 250 μg | 250 μg |
| TWEEN ® 20 polysorbate | 50 μg | 50 μg | 50 μg | 50 μg | 50 μg | 50 μg |
| Saccharose | 105 mg | — | — | — | — | — |
| Arginine | — | 33 mg | — | — | — | — |
| Glycine | — | — | 23 mg | — | — | — |
| Lysine | — | — | — | 28 mg | — | — |
| Sorbitol | — | — | — | — | 56.5 mg | — |
| Trehalose | — | — | — | — | — | 106 mg |
| WFI | q.s. to 1 ml | q.s. to 1 ml | q.s. to 1 ml | q.s. to 1 ml | q.s. to 1 ml | q.s. to 1 ml | q.s. = quantity sufficient

About 40 ml of each solution were prepared, filtered through a 0.22 μm membrane in a 22 ml stainless steel holder, and stored at 2-8° C., +25° C. and +40° C. in 15 ml plastic tubes. The solutions were tested for protein content (by SE-HPLC), oxidized forms (by RP-HPLC), aggregates (by SE-HPLC) and subunits formation (qualitatively, by SE-HPLC) up to 1 month. The results of the complete panel of tests applied to this set of formulations are reported in Tables 2 to 5.

TABLE 2

Purity by SE-HPLC (storage temperature: +40° C.)

| | % heterodimers | | | %free-subunits | | | % aggregates | | |
|---|---|---|---|---|---|---|---|---|---|
| Formulation | T = 0 | T = 1 d | T = 4 d | T = 0 | T = 1 d | T = 4 d | T = 0 | T = 1 d | T = 4 d |
| SAC/250 | 96.37 | 62.27 | 50.61 | 0.00 | 33.71 | 45.04 | 3.63 | 4.02 | 4.36 |
| GLY/250 | 95.29 | 56.55 | 42.55 | 0.00 | 36.42 | 54.04 | 4.71 | 6.43 | 3.42 |
| ARG/250 | 95.82 | 52.91 | 23.80 | 0.00 | 39.83 | 71.53 | 4.18 | 7.27 | 4.68 |
| LYS/250 | 95.66 | 63.26 | 36.55 | 0.00 | 32.57 | 59.85 | 4.35 | 4.18 | 3.60 |
| SOR/250 | 95.55 | 65.87 | 41.57 | 0.00 | 29.64 | 53.95 | 4.45 | 4.49 | 4.49 |
| TRE/250 | 92.73 | 58.22 | 42.41 | 0.00 | 32.62 | 48.63 | 7.28 | 9.16 | 8.97 |

T = time;

d = day(s)

TABLE 3

Purity by SE-HPLC (storage temperature: +25° C.)

| | % heterodimers | | | % free-subunits | | | % aggregates | | |
|---|---|---|---|---|---|---|---|---|---|
| Formulation | T = 0 | T = 7 d | T = 1 M | T = 0 | T = 7 d | T = 1 M | T = 0 | T = 7 d | T = 1 M |
| SAC/250 | 96.37 | 86.52 | 81.99 | 0.00 | — | 12.34 | 3.63 | 13.48 | 5.68 |
| GLY/250 | 95.29 | 97.41 | 78.52 | 0.00 | — | 18.64 | 4.71 | 2.59 | 2.84 |
| ARG/250 | 95.82 | 98.01 | 80.80 | 0.00 | — | 16.15 | 4.18 | 2.00 | 3.06 |
| LYS/250 | 95.66 | 99.20 | 80.83 | 0.00 | — | 17.19 | 4.35 | 0.81 | 1.99 |
| SOR/250 | 95.55 | 80.63 | 26.45 | 0.00 | 18.72 | 72.27 | 4.45 | 0.66 | 1.28 |
| TRE/250 | 92.73 | 95.29 | 74.86 | 0.00 | — | 17.24 | 7.28 | 4.71 | 7.91 |

M = month

TABLE 4

| | % oxidised forms by RP-HPLC | |
|---|---|---|
| Formulation | 12 days (+40° C.) | 1 Month (+25° C.) |
| SAC/250 | 7.62 | 21.84 |
| GLY/250 | 7.46 | n.a. |
| ARG/250 | 6.26 | 9.59 |
| LYS/250 | 6.68 | 4.90 |
| SOR/250 | 6.62 | 24.58 |
| TRE/250 | 19.95 | 10.45 | n.a. = not available

TABLE 5

| | r-hLH content by SE-HPLC | | | | |
|---|---|---|---|---|---|
| Formulation | T = 0 | T = 1 d (+40° C.) | T = 4 d (+40° C.) | T = 0 | T = 1 M (+25° C.) |
| SAC/250 | 5.50 | 4.20 | 4.50 | 5.50 | 5.40 |
| GLY/250 | 6.10 | 5.10 | 5.10 | 6.10 | 5.03 |
| ARG/250 | 6.30 | 6.70 | 6.40 | 6.30 | 6.33 |
| LYS/250 | 6.00 | 4.80 | 5.50 | 6.00 | 6.02 |
| SOR/250 | 5.30 | 4.80 | 5.10 | 5.30 | 4.93 |
| TRE/250 | 5.40 | 4.80 | 5.40 | 5.40 | 5.23 |

Based on these results, saccharose, lysine and arginine were selected as best excipients to be further investigated for their compatibility with an increasing amount (250 μg/ml and 500 μg/ml) of methionine as antioxidant. The composition of the tested solutions is reported in Table 6. It should be noted that these solutions have been prepared ex novo.

TABLE 6

Composition of r-hLH monodose formulations containing the selected stabilizing agents and different amount of methionine

| Components Amount/ml | SAC/250 | ARG/250 | LYS/250 | SAC/500 | ARG/500 | LYS/500 |
|---|---|---|---|---|---|---|
| r-hLH bulk | 6 μg | 6 μg | 6 μg | 6 μg | 6 μg | 6 μg |
| $Na_2HPO_4 \cdot 2H_2O$ | 1.65 mg | 1.65 mg | 1.65 mg | 1.65 mg | 1.65 mg | 1.65 mg |
| $NaH_2PO_4 \cdot H_2O$ | 0.104 mg | 0.104 mg | 0.104 mg | 0.104 mg | 0.104 mg | 0.104 mg |
| Methionine | 250 μg | 250 μg | 250 μg | 500 μg | 500 μg | 500 μg |
| TWEEN ® 20 polysorbate | 50 μg | 50 μg | 50 μg | 50 μg | 50 μg | 50 μg |
| Saccharose | 105 mg | — | — | 105 mg | — | — |
| Arginine | — | 33 mg | — | — | 33 mg | — |
| Lysine | — | — | 28 mg | — | — | 28 mg |
| WFI | q.s. to 1 ml | q.s. to 1 ml | q.s. to 1 ml | q.s. to 1 ml | q.s. to 1 ml | q.s. to 1 ml |

About 100 ml of each solution were prepared, filtered through a 0.22 μm membrane in a 22 ml stainless steel holder, and filled in 1 ml glass syringes to test also the compatibility between the drug substance and the final container (1 ml glass syringe+plunger). The syringes were stored at 2-8° C., +25° C., +33° C. and +40° C. The +33° C. storage temperature was introduced in order to have a compromise between a too fast (+40° C.) and a too low (+25° C.) degradation kinetic. The solutions were tested for r-hLH content (by SE-HPLC), oxidized forms (by RP-HPLC), aggregates (by SE-HPLC) and subunits formation (qualitatively, by SE-HPLC) up to 2-3 months.

The results of the complete panel of test applied to the formulations described in Table 6 are reported in Tables 7 to 11.

TABLE 7

Purity by SE-HPLC (storage temperature: +40° C.)

| | % heterodimers | | % free-subunits | | % aggregates | | % heterodimers (2-8° C.) | |
|---|---|---|---|---|---|---|---|---|
| Formulation | T = 0 | T = 4 d | T = 0 | T = 4 d | T = 0 | T = 4 d | T = 0 | T = 13 w |
| SAC/250 | 99.12 | 38.98 | — | 60.29 | 0.89 | 0.74 | 99.12 | 97.96 |
| ARG/250 | 98.30 | 9.16 | — | 90.03 | 1.70 | 0.83 | 98.30 | 99.23 |
| LYS/250 | 98.59 | 18.27 | — | 81.02 | 1.41 | 0.72 | 98.59 | 99.69 |
| SAC/500 | 99.34 | 33.96 | — | 64.11 | 0.66 | 1.93 | 99.34 | 98.66 |
| ARG/500 | 98.41 | 13.49 | — | 85.94 | 1.59 | 0.57 | 98.41 | 99.36 |
| LYS/500 | 98.72 | 29.07 | — | 69.89 | 1.22 | 1.05 | 98.72 | 99.68 | w = weeks

TABLE 8

Purity by SE-HPLC (storage temperature: +33° C.)

| | % heterodimers | | | | | % free-subunits | | | | |
|---|---|---|---|---|---|---|---|---|---|---|
| Formulation | T = 0 | T = 6 d | T = 4 w | T = 6 w | T = 8 w | T = 0 | T = 6 d | T = 4 w | T = 6 w | T = 8 w |
| SAC/250 | 99.12 | 69.75 | 65.46 | 64.82 | n.a. | — | 29.25 | 46.04 | 32.49 | n.a. |
| ARG/250 | 98.30 | 65.03 | 39.69 | 37.00 | 31.37 | — | 32.20 | 58.05 | 61.22 | 63.90 |
| LYS/250 | 98.52 | 74.96 | 53.95 | 46.28 | 43.23 | — | 23.59 | 44.42 | 52.58 | 55.09 |
| SAC/500 | 99.34 | 71.26 | 43.14 | 27.77 | n.a. | — | 27.12 | 50.74 | 52.34 | n.a. |
| ARG/500 | 98.41 | 67.04 | 38.04 | 32.62 | 25.34 | — | 31.14 | 58.48 | 65.37 | 70.81 |
| LYS/500 | 98.72 | 74.03 | 52.81 | 49.17 | 43.88 | — | 24.88 | 45.07 | 49.04 | 53.24 |

| | % aggregates | | | | |
|---|---|---|---|---|---|
| Formulation | T = 0 | T = 6 d | T = 4 w | T = 6 w | T = 8 w |
| SAC/250 | 0.89 | 1.01 | n.a. | 2.70 | n.a. |
| ARG/250 | 1.70 | 2.77 | 2.26 | 1.79 | 4.74 |
| LYS/250 | 1.41 | 1.45 | 1.64 | 1.14 | 1.69 |
| SAC/500 | 0.66 | 1.63 | 19.90 | 6.12 | n.a. |
| ARG/500 | 1.59 | 1.83 | 3.48 | 2.02 | 3.86 |
| LYS/500 | 1.22 | 1.09 | 2.12 | 1.79 | 2.85 |

TABLE 9

Purity by SE-HPLC (storage temperature: +25° C.)

| | % heterodimers | | | % free-subunits | | | % aggregates | | |
|---|---|---|---|---|---|---|---|---|---|
| Formulation | T = 0 | T = 4 w | T = 8 w | T = 0 | T = 4 w | T = 8 w | T = 0 | T = 4 w | T = 8 w |
| SAC/250 | 99.12 | 98.36 | 76.81 | — | — | 21.05 | 0.89 | 1.65 | 2.15 |
| ARG/250 | 98.30 | 79.80 | 73.39 | — | 17.89 | 23.99 | 1.70 | 2.32 | 2.63 |
| LYS/250 | 98.59 | 84.15 | 77.60 | — | 13.78 | 21.23 | 1.41 | n.a. | 1.18 |
| SAC/500 | 99.34 | n.a. | 61.24 | — | n.a. | 33.50 | 0.66 | n.a. | 5.26 |
| ARG/500 | 98.41 | n.a. | 69.45 | — | n.a. | 27.93 | 1.59 | n.a. | 2.63 |
| LYS/500 | 98.72 | n.a. | 78.56 | — | n.a. | 19.81 | 1.22 | n.a. | 1.64 |

TABLE 10

% oxidised forms by RP-HPLC

| Formulation | 4 days (+40° C.) | 8 weeks (+25° C.) | 4 weeks (+33° C.) | 6 weeks (+33° C.) |
|---|---|---|---|---|
| SAC/250 | 6.13 | 7.32 | 9.72 | 20.13 |
| SAC/500 | 17.37 | 35.78 | 39.12 | 45.93 |
| ARG/250 | 6.29 | 5.96 | 9.72 | 7.02 |
| ARG/500 | 4.69 | 5.67 | 6.69 | 8.10 |
| LYS/250 | 5.24 | 5.05 | 8.00 | 8.63 |
| LYS/500 | 3.25 | 4.02 | 5.71 | 6.84 |

TABLE 11 r-hLH content by SE-HPLC

| Formulation | T = 0 | T = 4 days (+40° C.) | T = 8 weeks (+25° C.) | T = 4 weeks (+33° C.) | T = 6 weeks (+33° C.) | T = 8 weeks (+33° C.) |
|---|---|---|---|---|---|---|
| SAC/250 | 5.03 | 3.09 | 5.09 | 5.31 | 4.74 | n.a. |
| SAC/500 | 6.27 | 4.92 | 6.00 | 5.96 | 5.63 | 6.20 |
| ARG/250 | 5.90 | 3.74 | 5.50 | 5.63 | 5.34 | 5.17 |
| ARG/500 | 5.00 | 3.36 | 4.25 | 5.05 | n.a. | n.a. |
| LYS/250 | 6.14 | 4.54 | 5.74 | 5.83 | 5.58 | 5.84 |
| LYS/500 | 6.08 | 3.91 | 5.61 | 5.73 | 5.49 | 5.48 |

Based on these results saccharose showed a higher compatibility with 250 µg/ml of methionine, lysine with 500 µg/ml of methionine and arginine with both concentrations of methionine.

Example 2

Compatibility of r-hLH Monodose Liquid Formulations with FSH Multidose Liquid Formulation In view of the results disclosed in Example 1, the formulations described in Table 6 were mixed with an FSH formulation (i.e. Gonal-F® multidose liquid formulation) and tested after 24 h of contact at 25° C. according to the methods below:
RP-HPLC for r-hFSH and r-hLH α-subunit oxidised forms (in Table 12 under % purity the non-oxidised forms are reported)
SE-HPLC for aggregates quantitation
RP-HPLC for r-hFSH and r-hLH titre,
r-hFSH and r-hLH in vivo bioassay
SDS-PAGE for r-hFSH and r-hLH free-subunits and aggregates quantitation (data not reported),
Visual appearance.
The results are reported in Tables 12 to 14.

TABLE 12

Purity by RP-HPLC and % aggregates by SE-HPLC

| | % purity | | % aggregates | |
|---|---|---|---|---|
| Formulation | T = 0 | T = 24 h | T = 0 | T = 24 h |
| SAC/250 | 98.53 | 98.61 | 0.00 | 0.00 |
| ARG/250 | 97.29 | 99.17 | 0.00 | 0.72 |
| LYS/250 | 97.81 | 97.73 | 0.00 | 0.37 |
| SAC/500 | 98.50 | 98.17 | 0.00 | 0.39 |
| ARG/500 | 97.75 | 97.47 | 0.00 | 0.69 |
| LYS/500 | 97.04 | 96.74 | 0.00 | 0.33 | h = hours

TABLE 13

FSH and LH content

| | r-hFSH content* | | r-hLH content# | |
|---|---|---|---|---|
| Formulation | T = 0 | T = 24 h | T = 0 | T = 24 h |
| SAC/250 | 16.14 | 16.14 | 3.67 | 3.61 |
| ARG/250 | 15.45 | 16.01 | 4.15 | 4.21 |
| LYS/250 | 15.35 | 15.68 | 4.07 | 4.15 |
| SAC/500 | 16.29 | 16.91 | 3.71 | 3.70 |
| ARG/500 | 16.03 | 15.80 | 4.15 | 4.05 |
| LYS/500 | 15.46 | 15.69 | 4.05 | 4.17 |

*FSH theoretical: 200 IU = 15.48 µg/ml;
LH theoretical: 100 IU = 4 µg/ml

TABLE 14

Bioassay

| | r-hFSH activity | | r-hLH activity | |
|---|---|---|---|---|
| Formulation | T = 0 | T = 24 h | T = 0 | T = 24 h |
| SAC/250 | 174.60 | 183.70 | 108.00 | 109.00 |

All the tested monodose formulations were compatible with the Gonal-F® multidose formulation as there was:
No loss in FSH and LH content,
No oxidation,
No aggregation and free-subunits dissociation (by SDS-PAGE)
No loss in LH and FSH bioactivity.

Example 3

Stability Study of Monodose Liquid Formulations

On the basis of the results of the previous examples, the formulations described in Table 6, except those containing arginine, were prepared at two different r-hLH concentrations (6 µg/ml and 12 µg/ml), stored at 2-8° C. and +25° C. and tested according to a rigorous stability plan and according to the following analytical methods:

RP-HPLC for LH content
RP-HPLC for α-subunit oxidised forms
SDS-PAGE for free-subunits and aggregates
Bioassay
pH of solution
Visual appearance A statistical analysis was performed on the results of all the parameters that were identified as stability indicating with the aid of Stabileo 1.1 software.

r-hLH Concentration (by RP-HPLC) Upon Storage at 2-8° C. and 25±2° C.

No statistically significant loss in protein concentration was observed for the formulations after 6-months storage at 2-8° C. whatever the r-hLH concentration (6 μg/ml and 12 μg/ml). A common decrease of 0.4 μg/month was observed after 6-months storage at 25±2° C.

r-hLH Bioactivity (Bioassay) Upon Storage at 2-8° C. and 25±2° C.

No relevant loss in bioactivity was observed for the formulations after 6-months storage at 2-8° C. and at 25±2° C. whatever the r-hLH concentration (6 μg/ml and 12 μg/ml).

% Subunits and Aggregates by SDS-PAGE

The percentage of aggregates by SDS-PAGE remains below 2% for both concentrations after 6-months storage at 2-8° C. and 25° C. The percentage of subunits by SDS-PAGE remains below 2% for both concentrations after 6-months storage at 2-8° C. A common decrease of about 5%/month was observed after 6-months storage at 25° C.±2° C.

% Oxidised Forms by RP-HPLC

An increase of about 0.4%/month was measured after 6-months storage at 2-8° C. and an increase in the range 0.6-1.4%/month at 25° C.±2° C.

pH and Appearance

No change in the appearance (colour, clarity, visible particles) nor in the pH was observed during manufacturing and upon storage.

Example 4

Compatibility of Stabilizing and Bacteriostatic Agents for Multidose Formulations Six stabilizing agents (saccharose, arginine, glycine, lysine, sorbitol and trehalose) were tested for compatibility with bacteriostatic agents to deliver stable multidose formulations. The tested formulations are summarized in Table 15.

TABLE 15

Composition of several r-hLH multidose formulations containing different combinations of stabilizing and bacteriostatic agents

| Components Amount/ml | SAC/250 BA | SAC/250 mCr | SAC/250 Phe | ARG/250 BA | ARG/250 mCr | ARG/250 Phe |
|---|---|---|---|---|---|---|
| r-hLH bulk | 25 μg | 25 μg | 25 μg | 25 μg | 25 μg | 25 μg |
| $Na_2HPO_4\,2H_2O$ | 1.65 mg | 1.65 mg | 1.65 mg | 1.65 mg | 1.65 mg | 1.65 mg |
| $NaH_2PO_4\,H_2O$ | 0.104 mg | 0.104 mg | 0.104 mg | 0.104 mg | 0.104 mg | 0.104 mg |
| Methionine | 250 μg | 250 μg | 250 μg | 250 μg | 250 μg | 250 μg |
| TWEEN ® 20 polysorbate | 50 μg | 50 μg | 50 μg | 50 μg | 50 μg | 50 μg |
| Saccharose | 105 mg | 105 mg | 105 mg | — | — | — |
| Arginine | — | — | — | 33 mg | 33 mg | 33 mg |
| Benzyl Alcohol | 0.90% | — | — | 0.90% | — | — |
| m-Cresol | — | 0.30% | — | — | 0.30% | — |
| Phenol | — | — | 0.50% | — | — | 0.50% |
| WFI | q.s. to 1 ml | q.s. to 1 ml | q.s. to 1 ml | q.s. to 1 ml | q.s. to 1 ml | q.s. to 1 ml |

| Components Amount/ml | LYS/250 BA | LYS/250 mCr | LYS/250 Phe | SOR/250 BA | SOR/250 mCr | SOR/250 Phe |
|---|---|---|---|---|---|---|
| r-hLH bulk | 25 μg | 25 μg | 25 μg | 25 μg | 25 μg | 25 μg |
| $Na_2HPO_4\,2H_2O$ | 1.65 mg | 1.65 mg | 1.65 mg | 1.65 mg | 1.65 mg | 1.65 mg |
| $NaH_2PO_4\,H_2O$ | 0.104 mg | 0.104 mg | 0.104 mg | 0.104 mg | 0.104 mg | 0.104 mg |
| Methionine | 250 μg | 250 μg | 250 μg | 250 μg | 250 μg | 250 μg |
| TWEEN ® 20 polysorbate | 50 μg | 50 μg | 50 μg | 50 μg | 50 μg | 50 μg |
| Lysine | 28 mg | 28 mg | 28 mg | — | — | — |
| Sorbitol | — | — | — | 56.5 mg | 56.5 mg | 56.5 mg |
| Benzyl Alcohol | 0.90% | — | — | 0.90% | — | — |
| m-Cresol | — | 0.30% | — | — | 0.30% | — |
| Phenol | — | — | 0.50% | — | — | 0.50% |
| WFI | q.s. to 1 ml | q.s. to 1 ml | q.s. to 1 ml | q.s. to 1 ml | q.s. to 1 ml | q.s. to 1 ml |

| Components Amount/ml | GLY/250/ BA | GLY/250/ mCr | GLY/250/ Phe | TRE/250/ BA | TRE/250/ mCr | TRE/250/ Phe |
|---|---|---|---|---|---|---|
| r-hLH bulk | 25 μg | 25 μg | 25 μg | 25 μg | 25 μg | 25 μg |
| $Na_2HPO_4\,2H_2O$ | 1.65 mg | 1.65 mg | 1.65 mg | 1.65 mg | 1.65 mg | 1.65 mg |
| $NaH_2PO_4\,H_2O$ | 0.104 mg | 0.104 mg | 0.104 mg | 0.104 mg | 0.104 mg | 0.104 mg |
| Methionine | 250 μg | 250 μg | 250 μg | 250 μg | 250 μg | 250 μg |
| TWEEN ® 20 polysorbate | 50 μg | 50 μg | 50 μg | 50 μg | 50 μg | 50 μg |
| Glycine | 23 mg | 23 mg | 23 mg | — | — | — |
| Trehalose | — | — | — | 106 mg | 106 mg | 106 mg |

TABLE 15-continued

Composition of several r-hLH multidose formulations containing different combinations of stabilizing and bacteriostatic agents

| Benzyl Alcohol | 0.90% | — | — | 0.90% | — | — |
|---|---|---|---|---|---|---|
| m-Cresol | — | 0.30% | — | — | 0.30% | — |
| Phenol | — | — | 0.50% | — | — | 0.50% |
| WFI | q.s. to 1 ml | q.s. to 1 ml | q.s. to 1 ml | q.s. to 1 ml | q.s. to 1 ml | q.s. to 1 ml |

About 40 ml of each solution were prepared, filtered through a 0.22 µm membrane and stored at 2-8° C., +25° C. and +40° C. in 15 ml plastic tubes. The solutions were tested for protein content (by Size Exclusion-HPLC, SE-HPLC, data not shown), oxidized forms (by Reverse Phase-HPLC, RH-HPLC), aggregates (by SE-HPLC) and subunits formation (qualitatively, by SE-HPLC) up to 1 month. The results of the complete panel of tests applied to this set of formulations are reported in Tables 16 to 18. All the solutions containing m-Cresol (mCr) became opalescent even immediately after manufacturing, due to an incompatibility between the bacteriostatic agent and the polysorbate surfactant (TWEEN® 20).

TABLE 16

Purity by SE-HPLC (storage temperature: +40° C.)

| | % heterodimers | | | % free-subunits | | | % aggregates | | |
|---|---|---|---|---|---|---|---|---|---|
| Formulation | T = 0 | T = 1 d | T = 4 d | T = 0 | T = 1 d | T = 4 d | T = 0 | T = 1 d | T = 4 d |
| SAC/250/mCr | 98.91 | 89.61 | 52.93 | — | n.a. | 23.67 | 1.10 | 10.38 | 23.41 |
| SAC/250/BA | 95.50 | 74.04 | 51.52 | — | 22.65 | 45.12 | 4.50 | 3.33 | 3.36 |
| SAC/250/Phe | 98.34 | 74.20 | 67.13 | — | 19.63 | 23.71 | 1.66 | 5.57 | 9.17 |
| GLY/250/mCr | 97.95 | 96.54 | 86.76 | — | 9.55 | n.a. | 2.05 | 3.14 | n.a. |
| GLY/250/BA | 96.08 | 59.58 | 41.59 | — | 37.82 | 56.45 | 3.92 | 2.61 | 1.97 |
| GLY/250/Phe | 96.49 | 74.71 | 86.06 | — | 20.01 | 9.22 | 2.51 | 5.28 | 4.73 |
| ARG/250/mCr | 97.94 | 70.34 | 44.39 | — | 28.39 | 53.33 | 2.06 | 1.29 | 2.29 |
| ARG/250/BA | 91.44 | 35.99 | 15.91 | — | 58.99 | 79.65 | 8.57 | 5.03 | 4.45 |
| ARG/250/Phe | 95.31 | 63.27 | 29.12 | — | 33.75 | 67.18 | 4.69 | 2.98 | 3.70 |
| LYS/250/mCr | 98.19 | 81.57 | 65.68 | — | 17.99 | 33.10 | 1.81 | n.a. | 1.22 |
| LYS/250/BA | 94.75 | 47.94 | 33.61 | — | 48.59 | 63.14 | 5.26 | 3.48 | 3.26 |
| LYS/250/Phe | 97.91 | 72.68 | 56.73 | — | 26.18 | 42.26 | 2.09 | 1.16 | 1.01 |
| SOR/250/mCr | 90.46 | 86.33 | 58.78 | — | n.a. | 18.87 | 9.55 | 13.68 | 22.36 |
| SOR/250/BA | 94.08 | 62.71 | 45.27 | — | 64.17 | 47.22 | 5.93 | 3.13 | 7.52 |
| SOR/250/Phe | 94.74 | 70.58 | 55.75 | — | 22.30 | 32.76 | 5.26 | 7.13 | 11.50 |
| TRE/250/mCr | 86.07 | 77.26 | 40.60 | — | n.a. | 20.87 | 13.93 | 22.74 | 38.53 |
| TRE/250/BA | 94.74 | 69.53 | 42.19 | — | 21.36 | 44.22 | 5.26 | 9.12 | 12.88 |
| TRE/250/Phe | 91.05 | 85.29 | 54.89 | — | n.a. | 24.28 | 8.95 | 14.72 | 20.83 |

TABLE 17

Purity by SE-HPLC (storage temperature: +25° C.)

| | % heterodimers | | | % free-subunits | | | % aggregates | | |
|---|---|---|---|---|---|---|---|---|---|
| Formulation | T = 0 | T = 7 d | T = 1 M | T = 0 | T = 7 d | T = 1 M | T = 0 | T = 7 d | T = 1 M |
| SAC/250/mCr | 98.91 | 53.76 | 69.30 | — | 31.19 | 15.13 | 1.10 | 14.34 | 15.57 |
| SAC/250/BA | 95.50 | 95.04 | 75.84 | — | — | 14.66 | 4.50 | 4.96 | 9.50 |
| SAC/250/Phe | 98.34 | 93.82 | 85.49 | — | — | — | 1.66 | 6.18 | 14.51 |
| GLY/250/mCr | 97.95 | 97.00 | 95.39 | — | — | — | 2.05 | 3.00 | 4.62 |
| GLY/250/BA | 96.08 | 97.63 | 68.21 | — | — | 28.42 | 3.92 | 2.37 | 2.17 |
| GLY/250/Phe | 96.49 | 97.44 | 93.19 | — | — | — | 2.51 | 2.57 | 6.10 |
| ARG/250/mCr | 97.94 | 98.73 | 78.33 | — | — | 19.73 | 2.06 | 1.28 | 1.94 |
| ARG/250/BA | 91.44 | 97.38 | 79.79 | — | — | 18.91 | 8.57 | 2.63 | 1.31 |
| ARG/250/Phe | 95.31 | 98.33 | 82.18 | — | — | 16.59 | 4.69 | 1.67 | 1.23 |
| LYS/250/mCr | 98.19 | 98.28 | 95.38 | — | — | — | 1.81 | 1.73 | 4.27 |
| LYS/250/BA | 94.75 | 97.39 | 82.54 | — | — | 14.66 | 5.26 | 2.61 | 2.80 |
| LYS/250/Phe | 97.91 | 99.55 | 98.61 | — | — | — | 2.09 | 0.46 | 1.40 |
| SOR/250/mCr | 90.46 | 82.65 | 64.24 | — | — | — | 9.55 | 17.23 | 35.76 |
| SOR/250/BA | 94.08 | 95.93 | 68.59 | — | — | 21.99 | 5.93 | 4.08 | 9.43 |
| SOR/250/Phe | 94.74 | 92.55 | 81.96 | — | — | — | 5.26 | 7.46 | 18.05 |
| TRE/250/mCr | 86.07 | 75.78 | 45.61 | — | — | — | 13.93 | 24.23 | 54.40 |
| TRE/250/BA | 94.74 | 91.22 | 67.28 | — | — | 13.75 | 5.26 | 8.79 | 18.97 |
| TRE/250/Phe | 91.05 | 84.53 | 66.79 | — | — | — | 8.95 | 15.47 | 33.22 |

TABLE 18

| Formulation | % oxidised forms by RP-HPLC | |
|---|---|---|
| | 12 days (+40° C.) | 1 Month (+25° C.) |
| SAC/250/mCr | 51.14 | 16.62 |
| SAC/250/BA | 14.07 | 8.83 |
| SAC/250/Phe | 25.55 | 17.54 |
| GLY/250/mCr | 59.29 | 5.43 |
| GLY/250/BA | 10.53 | 4.44 |
| GLY/250/Phe | 34.86 | 16.06 |
| ARG/250/mCr | 65.27 | 3.13 |
| ARG/250/BA | 7.12 | 5.65 |
| ARG/250/Phe | 15.49 | 11.27 |
| LYS/250/mCr | 44.05 | 16.36 |
| LYS/250/BA | 13.69 | 9.30 |
| LYS/250/Phe | 56.55 | 17.86 |
| SOR/250/mCr | 58.29 | 25.68 |
| SOR/250/BA | 13.51 | 8.49 |
| SOR/250/Phe | 30.78 | 17.75 |
| TRE/250/mCr | 45.84 | 26.36 |
| TRE/250/BA | 19.12 | 11.41 |
| TRE/250/Phe | 23.87 | 27.76 |

Based on these results, saccharose, lysine and arginine were selected as the best stabilizing agents to be further investigated for their compatibility with an increased amount of methionine (500 µg/ml). Benzyl alcohol, phenol and a combination of benzyl alcohol and benzalkonium chloride were selected as bacteriostatic agents. The tested formulations are summarized in Table 19.

TABLE 19

Composition of several r-hLH multidose formulations containing the selected stabilizing agents and different bacteriostatic agents

| Components Amount/ml | SAC/500 BA | SAC/500 BACL | SAC/500 Phe | ARG/500 BA | ARG/500 BACL | ARG/500 Phe |
|---|---|---|---|---|---|---|
| r-hLH bulk | 25 µg | 25 µg | 25 µg | 25 µg | 25 µg | 25 µg |
| $Na_2HPO_4\ 2H_2O$ | 1.65 mg | 1.65 mg | 1.65 mg | 1.65 mg | 1.65 mg | 1.65 mg |
| $NaH_2PO_4\ H_2O$ | 0.104 mg | 0.104 mg | 0.104 mg | 0.104 mg | 0.104 mg | 0.104 mg |
| Methionine | 500 µg | 500 µg | 500 µg | 500 µg | 500 µg | 500 µg |
| TWEEN ® 20 polysorbate | 50 µg | 50 µg | 50 µg | 50 µg | 50 µg | 50 µg |
| Saccharose | 105 mg | 105 mg | 105 mg | — | — | — |
| Arginine | — | — | — | 33 mg | 33 mg | 33 mg |
| Benzyl Alcohol | 1.2% | 0.30% | — | 1.2% | 0.30% | — |
| Benzalkonium chloride | — | 0.001% | — | — | 0.001% | — |
| Phenol | — | — | 0.50% | — | — | 0.50% |
| WFI | q.s. to 1 ml | q.s. to 1 ml | q.s. to 1 ml | q.s. to 1 ml | q.s. to 1 ml | q.s. to 1 ml |

| Components Amount/ml | LYS/500/BA | LYS/500/BACL | LYS/500/Phe |
|---|---|---|---|
| r-hLH bulk | 25 µg | 25 µg | 25 µg |
| $Na_2HPO_4\ 2H_2O$ | 1.65 mg | 1.65 mg | 1.65 mg |
| $NaH_2PO_4\ H_2O$ | 0.104 mg | 0.104 mg | 0.104 mg |
| Methionine | 500 µg | 500 µg | 500 µg |
| TWEEN ® 20 polysorbate | 50 µg | 50 µg | 50 µg |
| Lysine | 28 mg | 28 mg | 28 mg |
| Benzyl Alcohol | 1.2% | 0.30% | — |
| Benzalkonium chloride | — | 0.001% | — |
| Phenol | — | — | 0.50% |
| WFI | q.s. to 1 ml | q.s. to 1 ml | q.s. to 1 ml |

About 100 ml of each solution were prepared, filtered through a 0.22 μm membrane and filled in 3 ml cartridges. The following primary packaging was used:
- 3 ml glass cartridges (Nuova Ompi) siliconised
- Crimp caps code CAP J 3ML L1H075-1-H1B FM 257/2 (Helvoet Pharma)
- Coated plungers: Helvoet V9282 FM257/2 Omniflex coated.

The cartridges were stored at 2-8° C., +25° C. and +40° C. to be tested for protein content (by SE-HPLC), oxidized forms (by RH-HPLC), aggregates (by SE-HPLC) and sub-units formation (qualitatively, by SE-HPLC) up to 2 months.

The results of the complete panel of tests applied to this second set of formulations are reported in Tables 20 to 26.

TABLE 20

Purity by SE-HPLC (storage temperature: +40° C.)

| Formulation | % heterodimers | | % free-subunits | | % ggregates | |
|---|---|---|---|---|---|---|
| | T = 0 | T = 3 days | T = 0 | T = 3 days | T = 0 | T = 3 days |
| SAC/500/BA | 100.00 | 60.01 | — | 39.55 | — | 0.44 |
| SAC/500/BACL | 100.00 | 67.39 | — | 32.34 | — | 0.27 |
| SAC/500/Phe | 99.66 | 65.01 | — | 31.27 | 0.34 | 3.72 |
| ARG/500/BA | 99.91 | 45.63 | — | 54.65 | 0.10 | — |
| ARG/500/BACL | 99.93 | 44.67 | — | 55.33 | 0.07 | — |
| ARG/500/Phe | 99.93 | 61.97 | — | 38.03 | 0.08 | — |
| LYS/500/BA | 99.93 | 61.71 | — | 38.30 | 0.08 | — |
| LYS/500/BACL | 99.95 | 61.33 | — | 38.68 | 0.06 | — |
| LYS/500/Phe | 99.93 | 76.03 | — | 23.59 | 0.08 | 0.39 |

TABLE 21

Purity by SE-HPLC (storage temperature: +33° C.)

| Formulation | % heterodimers | | | | % free-subunits | | | % aggregates | |
|---|---|---|---|---|---|---|---|---|---|
| | T = 0 | T = 3 w | T = 4 w | T = 8 w | T = 0 | T = 3 w | T = 4 w | T = 0 | T = 3 w |
| SAC/500/BA | 100.00 | 76.56 | 71.22 | 59.22 | — | 22.03 | 26.35 | / | 1.43 |
| SAC/500/BACL | 100.00 | 81.49 | 78.95 | 63.53 | — | 17.26 | 20.10 | / | 1.26 |
| SAC/500/Phe | 99.66 | 76.24 | 67.13 | 51.10 | — | 14.26 | 18.03 | 0.34 | 9.51 |
| ARG/500/BA | 99.91 | 71.90 | 71.52 | 61.41 | — | 27.89 | 27.73 | 0.10 | 0.21 |
| ARG/500/BACL | 99.93 | 69.08 | 66.86 | 57.22 | — | 30.67 | 32.94 | 0.07 | 0.26 |
| ARG/500/Phe | 99.93 | 86.11 | 76.74 | 75.51 | — | 13.76 | 22.55 | 0.08 | 0.14 |
| LYS/500/BA | 99.93 | 83.09 | 76.72 | 67.30 | — | 16.76 | 22.50 | 0.08 | 0.16 |
| LYS/500/BACL | 99.95 | 81.03 | 75.21 | 70.20 | — | 18.88 | 24.64 | 0.06 | 0.09 |
| LYS/500/Phe | 99.93 | 87.29 | 80.51 | 68.85 | — | 12.10 | 18.53 | 0.08 | 0.62 |

TABLE 22

Purity by SE-HPLC (storage temperature: +25° C.)

| Formulation | % heterodimers | | | % free-subunits | | % aggregates |
|---|---|---|---|---|---|---|
| | T = 0 | T = 4 w | T = 8 w | T = 0 | T = 4 w | T = 0 |
| SAC/500/BA | 100.00 | 83.85 | 82.87 | — | 14.69 | — |
| SAC/500/BACL | 100.00 | 86.30 | 85.78 | — | 13.06 | — |
| SAC/500/Phe | 99.66 | 79.35 | 75.26 | — | 13.39 | 0.34 |
| ARG/500/BA | 99.91 | 82.32 | 82.13 | — | 17.39 | 0.10 |
| ARG/500/BACL | 99.93 | 80.42 | 80.77 | — | 19.25 | 0.07 |
| ARG/500/Phe | 99.93 | 84.59 | 80.95 | — | 15.13 | 0.08 |
| LYS/500/BA | 99.93 | 85.04 | 85.10 | — | 13.78 | 0.08 |
| LYS/500/BACL | 99.95 | 84.24 | 86.22 | — | 15.42 | 0.06 |
| LYS/500/Phe | 99.93 | 85.41 | 81.22 | — | 13.68 | 0.08 |

TABLE 23

% oxidised forms by RP-HPLC (storage temperature: +33° C.)

| Formulation | T = 0 | T = 3 weeks | T = 8 weeks | T = 13 weeks |
|---|---|---|---|---|
| SAC/500/BA | 1.12 | 5.21 | 4.21 | 4.26 |
| SAC/500/BACL | 0.90 | 5.59 | 4.90 | 4.46 |
| SAC/500/Phe | 0.99 | 8.28 | 6.01 | 16.14 |
| ARG/500/BA | 0.69 | 4.52 | 4.13 | 2.65 |
| ARG/500/BACL | 1.13 | 4.57 | 3.57 | 2.97 |
| ARG/500/Phe | 0.94 | 4.60 | 5.24 | 4.82 |
| LYS/500/BA | 1.53 | 5.71 | 16.34 | 8.77 |
| LYS/500/BACL | 1.60 | 4.49 | 5.83 | 5.70 |
| LYS/500/Phe | 0.66 | 9.66 | 34.97 | 25.51 |

TABLE 24

% oxidised forms by RP-HPLC (storage temperature: +25° C.)

| Formulation | T = 0 | T = 4 weeks | T = 8 weeks | T = 13 weeks |
|---|---|---|---|---|
| SAC/500/BA | 1.12 | 2.04 | 2.19 | 2.44 |
| SAC/500/BACL | 0.90 | 2.10 | 2.31 | 2.23 |
| SAC/500/Phe | 0.99 | 2.68 | 5.72 | 7.50 |
| ARG/500/BA | 0.69 | 1.40 | 1.61 | 1.65 |
| ARG/500/BACL | 1.13 | 1.46 | 2.31 | 1.89 |
| ARG/500/Phe | 0.94 | 1.31 | 2.77 | 2.35 |
| LYS/500/BA | 1.53 | 2.51 | 3.35 | 4.73 |
| LYS/500/BACL | 1.60 | 1.96 | 3.14 | 3.47 |
| LYS/500/Phe | 0.66 | 4.05 | 11.38 | 22.52 |

TABLE 25

% oxidised forms by RP-HPLC

| Formulation | T = 0 | T = 13 weeks (+5° C.) | T = 0 | T = 3 days (+40° C.) |
|---|---|---|---|---|
| SAC/500/BA | 1.12 | 1.11 | 1.12 | 1.16 |
| SAC/500/BACL | 0.90 | 1.29 | 0.90 | 1.25 |
| SAC/500/Phe | 0.99 | 2.51 | 0.99 | 1.47 |
| ARG/500/BA | 0.69 | 1.03 | 0.69 | 0.64 |
| ARG/500/BACL | 1.13 | 1.16 | 1.13 | 1.06 |
| ARG/500/Phe | 0.94 | 2.02 | 0.94 | 1.47 |
| LYS/500/BA | 1.53 | 2.03 | 1.53 | 1.84 |
| LYS/500/BACL | 1.60 | 1.56 | 1.60 | 1.58 |
| LYS/500/Phe | 0.66 | n.a. | 0.66 | 3.10 |

TABLE 26 r-hLH content by SE-HPLC

| Formulation | T = 0 | T = 3 d (+40° C.) | T = 3 w (+33° C.) | T = 4 w (+33° C.) | T = 8 w (+33° C.) | T = 4 w (+25° C.) | T = 8 w (+25° C.) |
|---|---|---|---|---|---|---|---|
| SAC/500/BA | 20.38 | 21.70 | 21.05 | 22.54 | 16.47 | 23.70 | 18.43 |
| SAC/500/BACL | 21.73 | 22.06 | 21.31 | 22.64 | 18.77 | 23.65 | 18.10 |
| SAC/500/Phe | 21.24 | 21.49 | 21.02 | 22.53 | 20.71 | 22.66 | 17.23 |
| ARG/500/BA | 22.23 | 18.86 | 19.52 | 24.64 | 16.14 | 25.26 | 17.69 |
| ARG/500/BACL | 22.38 | 21.48 | 21.71 | 23.52 | 16.86 | 24.18 | 19.34 |
| ARG/500/Phe | 21.34 | 22.38 | 20.60 | 23.09 | 16.99 | 24.41 | 16.32 |
| LYS/500/BA | 20.33 | 20.93 | 18.85 | 22.10 | 14.93 | 24.24 | 17.36 |
| LYS/500/BACL | 23.83 | 21.78 | 20.68 | 23.44 | 15.50 | 24.07 | 18.60 |
| LYS/500/Phe | 21.34 | 21.05 | 20.20 | 21.89 | 16.50 | 22.99 | 16.56 |

These results confirmed the compatibility of the stabilizing agents with an increased amount of methionine (see Example 1). In addition the results showed that the bacteriostatic agents are compatible with 500 μg/ml of methionine.

Example 5

Compatibility of r-hLH Multidose Liquid Formulations with FSH Multidose Liquid Formulation Based on the results of Example 4, formulations of r-hLH in 3 ml cartridges were mixed with a FSH formulation (i.e. Gonal-F® multidose liquid formulation) and tested after 24 h of contact at 25° C. according to the methods below:
  SE-HPLC for purity
  RP-HPLC for r-hFSH and r-hLH titre,
  RP-HPLC for r-hFSH and r-hLH α-subunit oxidised forms,
  r-hFSH and r-hLH in vivo bioassay
  SDS-PAGE for r-hFSH and r-hLH free-subunits and aggregates quantitation (data not reported),
  pH of solution,
  Visual appearance.
The results are reported in Tables 27 to 29.

TABLE 27

Purity by SE-HPLC

| Formulation | % heterodimers | | % aggregates | |
|---|---|---|---|---|
| | T = 0 | T = 24 h | T = 0 | T = 24 h |
| SAC/500/BA | 98.28 | 98.41 | 0.30 | 1.09 |
| SAC/500/BACL | 98.85 | 99.66 | 0.00 | 0.43 |
| SAC/500/Phe | 98.18 | 97.68 | 0.27 | 0.54 |
| ARG/500/BA | 98.31 | 98.61 | 0.28 | 0.98 |
| ARG/500/BACL | 97.68 | 98.52 | 0.33 | 0.53 |
| ARG/500/Phe | 97.89 | 97.73 | 0.44 | 0.77 |
| LYS/500/BA | 97.35 | 97.51 | 0.38 | 1.09 |
| LYS/500/BACL | 97.97 | 98.82 | 0.28 | 0.81 |
| LYS/500/Phe | 98.29 | 98.40 | 0.37 | 1.01 |

TABLE 28

FSH and LH content

| Formulation | r-hFSH content* | | r-hLH content# | |
|---|---|---|---|---|
| | T = 0 | T = 24 h | T = 0 | T = 24 h |
| SAC/500/BACL | 29.50 | 31.15 | 7.20 | 8.31 |
| SAC/500/Phe | 30.88 | 31.28 | 7.34 | 7.54 |

TABLE 28-continued

FSH and LH content

| Formulation | r-hFSH content* | | r-hLH content# | |
|---|---|---|---|---|
| | T = 0 | T = 24 h | T = 0 | T = 24 h |
| ARG/500/BA | 30.46 | 31.00 | 8.02 | 8.44 |
| ARG/500/BACL | 32.23 | 32.84 | 7.12 | 7.40 |
| ARG/500/Phe | 30.07 | 31.06 | 7.78 | 8.05 |
| LYS/500/BA | 30.91 | 32.11 | 6.88 | 7.25 |
| LYS/500/BACL | 28.57 | 31.66 | 6.64 | 7.62 |
| LYS/500/Phe | 28.75 | 31.25 | 6.80 | 7.47 |

*FSH theorical: 200 IU = 30.96 μg/ml;
LH theorical: 100 IU = 8 μg/ml

TABLE 29

Bioassay

| Formulation | r-hFSH activity | | r-hLH activity | |
|---|---|---|---|---|
| | T = 0 | T = 24 h | T = 0 | T = 24 h |
| SAC/500/BACL | 365.7 | 355.0 | 227.0 | 212.7 |
| ARG/500/Phe | 387.5 | 393.0 | 231.4 | 243.0 |

All the tested multidose formulations are compatible with the Gonal-F® multidose formulation as there was:
  No loss in FSH and LH content,
  No oxidation,
  No aggregation (by SE-HPLC)
  No aggregates and subunits formation by SDS-PAGE
  No loss in LH and FSH bioactivity.

Example 6

Compatibility with Primary Packaging

Figure 2:
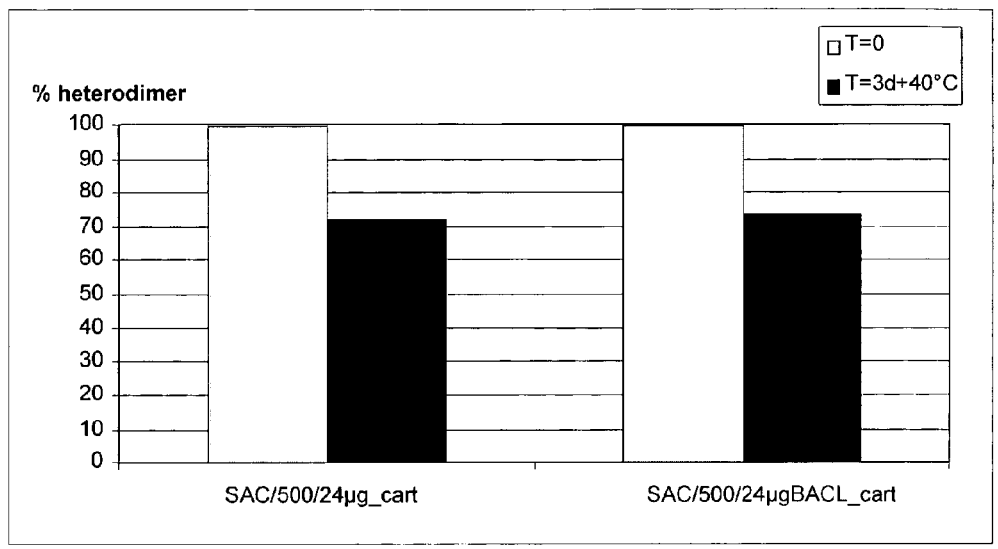
FIG. 2 shows the comparison of the percentage of heterodimers calculated by SE-HPLC on the formulation with and without the combination of bacteriostatic agents, respectively SAC/500/24 µgBACL_cart and SAC/500/24 µg_cart. (A) SE-HPLC performed after three days (3 d) with storage at +40° C. (B) SE-HPLC performed after eight days (8 d), four weeks (4 w), six weeks (6 w), eight weeks (8 w) and thirteen weeks (13 w) with storage at +33° C.
Figure 2:
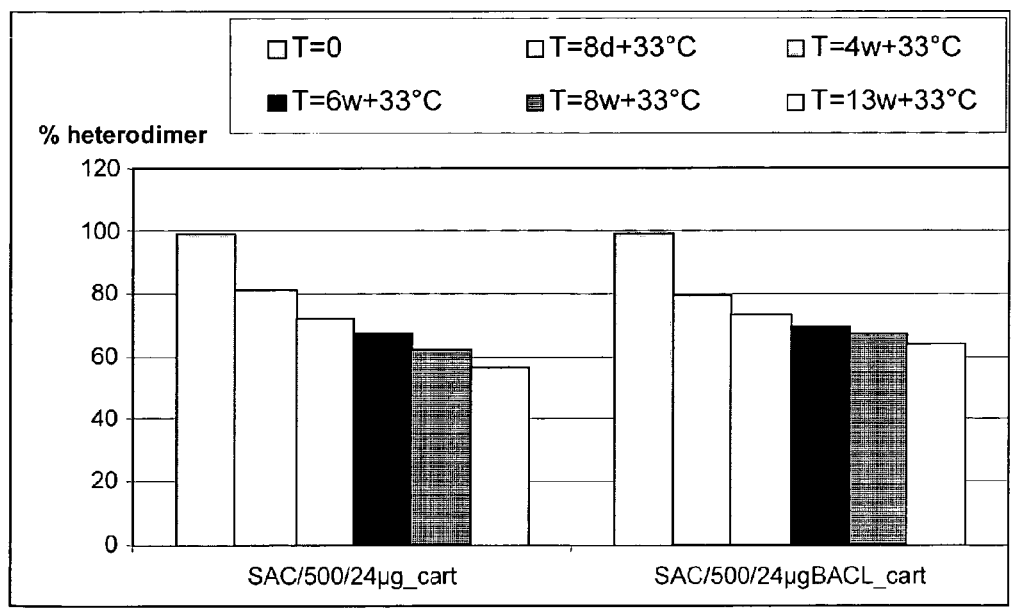

In order to test the compatibility between the r-hLH formulations and the final containers (syringes and cartridges), a matrix study was put in place to test the following parameters:
  Effect of r-hLH concentration: 6 μg/ml, 12 μg/ml, 24 μg/ml,
  Effect of filling volume: 0.25 ml, 0.5 ml, 1 ml,
  Type of container: 1 ml glass syringe and 3 ml glass cartridge,
  Effect of bacteriostatic agent: formulations prepared with and without the bacteriostatic agents and stored in 3 ml cartridges.
One formulation (SAC/500/BACL) was prepared at the different r-hLH strengths and filled in the containers at different filling volumes. The batches were compared qualitatively by SE-HPLC up to 1 week at +33° C. The results are reported in FIG. 1 (A-F). In FIG. 2 (A-B) the percentage of heterodimers by SE-HPLC on the formulation with and without the combination of bacteriostatic agents are compared. Looking at the results in FIGS. 1 and 2, the following conclusions can be drawn:

No impact of container on formulations at 12 µg/ml and 24 µg/ml

No impact of filling volume on formulations at 12 µg/ml and 24 µg/ml

Positive effect of increased concentration on subunits dissociation

No difference between batches with or without bacteriostatics

Higher stability is related to higher r-hLH concentration.

Example 7

Stability Study of Multidose Liquid Formulations

On the basis of the results of the previous examples, four formulations described in Table 19 (SAC/500/BACL, LYS/500/BA, LYS/500/BACL and ARG/500/Phe) were stored at 2-8° C. and +25° C. and tested according to a rigorous stability plan and according to the following analytical methods:
RP-HPLC for LH content
RP-HPLC for α-subunit oxidised forms
RP-HPLC for phenol content
RP-HPLC for benzalkonium chloride content
RP-HPLC for benzyl alcohol content
SDS-PAGE for free-subunits and aggregates
Bioassay
pH of solution
Visual appearance The lysine and arginine amount in the above formulations was adjusted (i.e. L-lysine monohydrochloride to 28.5 mg and L-arginine monohydrochloride to 31.5 mg) to optimize the isotonicity of the formulations.

A statistical analysis was performed on the results of all the parameters that were identified as stability indicating with the aid of Stabileo 1.1 software.

r-hLH Concentration (by RP-HPLC) Upon Storage at 2-8° C. and 25±2° C.

No statistically significant loss in protein concentration was observed for the formulations after 12-months storage at 2-8° C. A common decrease of 0.4 µg/month was observed after 6-months storage at 25±2° C.

r-hLH Bioactivity (Bioassay) Upon Storage at 2-8° C. and 25±2° C.

No relevant loss in bioactivity was observed for the formulations after 12-months storage at 2-8° C. and at 25±2° C.

% Subunits and Aggregates by SDS-PAGE

The percentage of aggregates by SDS-PAGE remains below 2% for all formulations after 12-months storage at 2-8° C. and 25° C.

The percentage of subunits by SDS-PAGE increases above 32% after 6 months at 25° C. for all the formulations.

% Oxidised Forms by RP-HPLC

SAC/500/BACL and ARG/500/Phe present the lower increase of oxidised forms.

pH and Appearance

No change in the appearance (colour, clarity, visible particles) nor in the pH was observed during manufacturing and upon storage.

Bacteriostatic Agents Content

The target amounts of phenol and benzyl alcohol were detected and no losses were measured from 6-months to 12-months stability checkpoints. An amount of benzalkonium chloride below target (6 µg/ml instead of 10 µg/ml) was measured in the SAC/500/BACL formulation at 6-months stability checkpoint.

Efficacy of Bacteriostatic Agents

The results of the bacteriostatic efficacy tests, performed at T=0 and repeated after 9 months on the formulations are reported in Tables 30 to 33.

TABLE 30

Results of bacteriostatic efficacy test on multidose formulation SAC/500/BACL

| | Log reduction vs T = 0 | | | | |
| --- | --- | --- | --- | --- | --- |
| Microrganism | T = 6 h | T = 24 h | T = 7 days | T = 14 days | T = 28 days |
| Staphylococcus aureus | >3 | >3 | >3 | >3 | no reduction |
| Pseudomonas aeruginosa | >3 | >3 | >3 | >3 | no reduction |
| Escherichia coli | no tested | n.t. | >3 | >3 | no reduction |
| Candida albicans | n.t. | n.t. | >3 | >3 | no increase |
| Aspergillus niger | n.t. | n.t. | 1.8 | >3 | no increase |

TABLE 31

Results of bacteriostatic efficacy test on multidose formulation LYS/500/BACL

| | Log reduction vs T = 0 | | | | |
| --- | --- | --- | --- | --- | --- |
| Microrganism | T = 6 h | T = 24 h | T = 7 days | T = 14 days | T = 28 days |
| Staphylococcus aureus | >3 | >3 | >3 | >3 | no reduction |
| Pseudomonas aeruginosa | >3 | >3 | >3 | >3 | no reduction |
| Escherichia coli | not tested | n.t. | >3 | >3 | no reduction |
| Candida albicans | n.t. | n.t. | >3 | >3 | no increase |
| Aspergillus niger | n.t. | n.t. | 3.3 | >3 | no increase |

TABLE 32

Results of bacteriostatic efficacy test on multidose formulation LYS/500/BA

| | Log reduction vs T = 0 | | | | |
| --- | --- | --- | --- | --- | --- |
| Microrganism | T = 6 h | T = 24 h | T = 7 days | T = 14 days | T = 28 days |
| Staphylococcus aureus | 1.05 | >3 | >3 | >3 | no reduction |
| Pseudomonas aeruginosa | >3 | >3 | >3 | >3 | no reduction |
| Escherichia coli | not tested | n.t. | >3 | >3 | no reduction |
| Candida albicans | n.t. | n.t. | >3 | >3 | no increase |
| Aspergillus niger | n.t. | n.t. | >3 | >3 | no increase |

TABLE 33

Results of bacteriostatic efficacy test on multidose formulation ARG/500/Phe

| Microorganism | Log reduction vs T = 0 | | | | |
|---|---|---|---|---|---|
| | T = 6 h | T = 24 h | T = 7 days | T = 14 days | T = 28 days |
| Staphylococcus aureus | 0.73 | >3 | >3 | >3 | no reduction |
| Pseudomonas aeruginosa | >3 | >3 | >3 | >3 | no reduction |
| Escherichia coli | not tested | n.t. | >3 | >3 | no reduction |
| Candida albicans | n.t. | n.t. | >3 | >3 | no increase |
| Aspergillus niger | n.t. | n.t. | >3 | >3 | no increase |

The formulations containing the combination of 0.3% benzyl alcohol+0.001% benzalkonium chloride, and saccharose or lysine (SAC/500/BACL and LYS/500/BACL) met Criteria A of the European Pharmacopeia even if the amount of benzalkonium chloride was below the target (6 µg/ml instead of 10 µg/ml).

The formulation containing 0.5% phenol (ARG/500/Phe) and the formulation containing 1.2% benzyl alcohol (LYS/500/BA) met Criteria B of the European Pharmacopeia.

CONCLUSIONS

All multidose formulations showed a good stability profile after 12 months storage at 2-8° C.

REFERENCES

Burgues et al.; Subcutaneous self-administration of highly purified follicle stimulating hormone and human chorionic gonadotrophin for the treatment of male hypogonadotrophic hypogonadism. Spanish Collaborative Group on Male Hypogonadotrophic Hypogonadism; *Hum. Reprod.;* 1997, 12(5): 980-6

Cerpa-Poljak et al.; Isoelectric charge of recombinant human follicle-stimulating hormone isoforms determines receptor affinity and in vitro bioactivity; *Endocrinology;* 1993, 132 (1): 351-356

Dias et al.; Receptor binding and functional properties of chimeric human follitropin prepared by an exchange between a small hydrophilic intercysteine loop of human follitropin and human lutropin; *J. Biol. Chem.;* 1994, 269 (41): 25289-25294

Fiddes & Talmadge; Structure, expression, and evolution of the genes for the human glycoprotein hormones; *Recent Prog. Horm. Res.;* 1984, 40: 43-78

Flack et al.; Site-directed mutagenesis defines the individual roles of the glycosylation sites on follicle-stimulating hormone; *J. Biol. Chem.;* 1994, 269(19): 14015-14020

Hakola et al.; Recombinant rat follicle-stimulating hormone; production by Chinese hamster ovary cells, purification and functional characterization; *Molecular and Cellular Endocrinology,* 1997, 127(1): 59-69

Keene et al.; Expression of biologically active human follitropin in Chinese hamster ovary cells; *J. Biol. Chem.;* 1989, 264(9): 4769-4775

Keutmann et al.; Structure of human luteinizing hormone beta subunit: evidence for related carboxyl-terminal sequence among certain peptide hormones; *Biochem. Biophys. Res. Commun.;* 1979, 90(3): 842-848

Klein et al.; Pharmacokinetics and pharmacodynamics of single-chain recombinant human follicle-stimulating hormone containing the human chorionic gonadotrophin carboxyterminal peptide in the rhesus monkey; *Fertility & Sterility;* 2002, 77(6): 1248-1255

Klein et al.; Development and characterization of a long-acting recombinant hFSH agonist; *Human Reprod.;* 2003, 18(1): 50-56

LaPolt et al.; Enhanced stimulation of follicle maturation and ovulatory potential by long acting follicle-stimulating hormone agonists with extended carboxyl-terminal peptides; *Endocrinology;* 1992, 131(6): 2514-2520

Reichert & Ramsey; Dissociation of human follicle-stimulating hormone. Comparison with luteinizing hormone; *J. Biol. Chem.;* 1975, 250(8): 3034-3040

Shome et al.; Human follicle stimulating hormone: first proposal for the amino acid sequence of the hormone-specific, beta subunit (hFSHb); *J. Clin. Endocrinol. Metab.,* 1974; 39(1):203-205

Shome, et al.; A reevaluation of the amino acid sequence of human follitropin beta-subunit; *J. Prot. Chem.;* 1988, 7(4): 325-339

Steelman et al.; Assay of the follicle stimulating hormone based on the augmentation with human chorionic gonadotrophin; *Endocrinology;* 1953, 53(6): 604-616

Talmadge et al.; Evolution of the genes for the beta subunits of human chorionic gonadotropin and luteinizing hormone; *Nature;* 1984, 307: 37-40;

Valove et al.; Receptor binding and signal transduction are dissociable functions requiring different sites on follicle-stimulating hormone; *Endocrinology;* 1994, 135(6): 2657-2661

Van Hell et al.; Effects of human menopausal gonadotrophin preparations in different bioassay methods; *Acta Endocrinologica;* 1964, 47: 409-418

EP 0 211 894
EP 0 448 146
EP 0 487 512
EP 0 505 500
EP 0 618 808
EP 0 814 841
EP 0 853 945
WO 85/01958
WO 98/58957
WO 00/04913
WO 01/58493
WO 2004/087213
WO 2004/105788
WO 2004/112826
U.S. Pat. No. 3,119,740
U.S. Pat. No. 5,767,067

The invention claimed is:

1. A liquid formulation comprising:
   at least 25 µg/ml of r-hLH,
   1.65 mg/ml of $Na_2HPO_4$ $2H_2O$,
   0.104 mg/ml of $NaH_2PO_4$ $H_2O$,
   31.5 mg/ml of L-arginine monohydrochloride,
   0.05 mg/ml of Polysorbate 20,
   0.5 mg/ml of methionine, and
   5 mg/ml of phenol.

2. A pharmaceutical composition comprising the formulation according to claim 1.

3. The formulation according to claim 1, further wherein said formulation is hermetically sealed under sterile conditions in a container suitable for storage prior to use.

4. The formulation according to claim 1 for the treatment of infertility in women and/or men.

5. A liquid formulation comprising:
at least 25 µg/ml of r-hLH,
1.65 mg/ml of $Na_2HPO_4\ 2H_2O$,
0.104 mg/ml of $NaH_2PO_4\ H_2O$,
28.5 mg/ml of lysine monohydrochloride,
0.05 mg/ml of Polysorbate 20,
0.5 mg/ml of methionine and
12 mg/ml of benzyl alcohol.

6. A pharmaceutical composition comprising the formulation according to claim 5.

7. The formulation according to claim 5, further wherein said formulation is hermetically sealed under sterile conditions in a container suitable for storage prior to use.

8. The formulation according to claim 5 for the treatment of infertility in women and/or men.

9. A liquid formulation comprising:
at least 25 µg/ml of r-hLH,
1.65 mg/ml of $Na_2HPO_4\ 2H_2O$,
0.104 mg/ml of $NaH_2PO_4\ H_2O$,
28.5 mg/ml of lysine monohydrochloride,
0.05 mg/ml of Polysorbate 20,
0.5 mg/ml of methionine 3 mg/ml of benzyl alcohol and
0.01 mg/ml of benzalkonium chloride.

10. A pharmaceutical composition comprising the formulation according to claim 9.

11. The formulation according to claim 9, further wherein said formulation is hermetically sealed under sterile conditions in a container suitable for storage prior to use.

12. The formulation according to claim 9 for the treatment of infertility in women and/or men.

13. A liquid formulation consisting essentially of:
luteinizing hormone (LH) or a variant thereof;
a phosphate buffer;
a stabilizing amount of an LH stabilizer selected from the group consisting of arginine and/or one or more salts thereof, at a concentration of 10 to 50 mg/ml;
Polysorbate 20;
methionine; and
phenol.

14. The formulation of claim 13 consisting essentially of:
1 to 50 µg/ml of luteinizing hormone (LH) or a variant thereof;
a phosphate buffer present at a concentration of 1 to 100 mM;
a stabilizing amount of an LH stabilizer selected from the group consisting of arginine and/or one or more salts thereof, at a concentration of 10 to 50 mg/ml;
Polysorbate 20 present at a concentration of 0.01 to 10 mg/ml;
methionine present at a concentration of 0.01 to 5.0 mg/ml; and
phenol at a concentration of 0.005 to 15 mg/ml.

15. The formulation according to claim 13 consisting essentially of:
at least 25 µg/ml of r-hLH;
1.65 mg/ml of $Na_2HPO_4\ 2H_2O$;
0.104 mg/ml of $NaH_2PO_4\ H_2O$;
31.5 mg/ml of L-arginine monohydrochloride;
0.05 mg/ml of Polysorbate 20;
0.5 mg/ml of methionine; and
5 mg/ml of phenol.

* * * * *